US007928187B2

(12) United States Patent
Kofler et al.

(10) Patent No.: US 7,928,187 B2
(45) Date of Patent: Apr. 19, 2011

(54) NEUROPEPTIDE ALARIN

(75) Inventors: Barbara Kofler, Salzburg (AT); Kerstin Moritz, Wals Siezenheim (AT); Katrin Fenninger, Salzburg (AT)

(73) Assignee: Austria Wirtschaftsservice Gesellschaft mit beschrankter Haftung, Vienna (AT)

( * ) Notice: Subject to any disclaimer, the term of this patent is extended or adjusted under 35 U.S.C. 154(b) by 0 days.

(21) Appl. No.: 11/908,080

(22) PCT Filed: Mar. 7, 2006

(86) PCT No.: PCT/EP2006/060506
§ 371 (c)(1),
(2), (4) Date: Sep. 7, 2007

(87) PCT Pub. No.: WO2006/094973
PCT Pub. Date: Sep. 14, 2006

(65) Prior Publication Data
US 2009/0149374 A1    Jun. 11, 2009

(30) Foreign Application Priority Data

Mar. 7, 2005  (AT) .................. A 382/2005

(51) Int. Cl.
A61K 38/00  (2006.01)
A61K 39/00  (2006.01)
C07K 16/00  (2006.01)
(52) U.S. Cl. .............. 530/324; 530/300; 424/185.1; 424/192.1; 424/198.1; 514/21.3
(58) Field of Classification Search .............. None
See application file for complete search history.

(56) References Cited

U.S. PATENT DOCUMENTS 6,703,491 B1 * 3/2004 Homburger et al. ......... 536/23.1
2004/0077531 A1   4/2004 Matsumoto et al.
2007/0107087 A1   5/2007 Nussaume et al.

FOREIGN PATENT DOCUMENTS

WO            02/074798 A3    9/2002
WO         2004/094589 A3    11/2004
WO      WO 2004/094589 A  *  11/2004

OTHER PUBLICATIONS

International Search Report and Written Opinion for PCT/EP2006/060506.
Austria Search Report for Application No. A 382/2005.
"Abstracts from the Summer Neuropeptide Conference: The 15th Annual Meeting of the Summer Neuropeptide Conference, Miami Beach, Florida, USA, Jul. 5-9, 2005," Neuropeptides (2006), 40:137-159.
"Abstracts XV European Neuropeptides Club Meeting, Riga, Latvia, May 19-21, 2005," Neuropeptides (2005), 39:595-632.
Cunningham, et al., "Cloning and Distribution of Galanin-Like Peptide mRNA in the Hypothalamus and Pituitary of the Macaque," Endocrinology (2002), 143:755-763.
Ohtaki, T., et al., Isolation and cDNA Cloning of a Novel Galanin-Like Peptide (GALP) from Porcine Hypothalamus,: J. Biol. Chem (1999), 52:37041-5.
Santic, R., et al., "Differential Splicing of the Human and Murine Galanin-Like Peptide Gene," Journal of Neurochemistry (2005), 94:184 (Abstract).
Unniappan, S., et al., "Characterization of Complementary Deoxyribonucleic Acids Encoding Preprogalanin and Its Alternative Splice Variants in the Goldfish," Mol Cell Endocrinol (2003), 200:177-87 (Abstract).

* cited by examiner

*Primary Examiner* — Olga N Chernyshev
(74) *Attorney, Agent, or Firm* — Chainey P. Singleton; Edwin S. Flores; Daniel J. Chalker

(57) ABSTRACT

The present invention describes a polypeptide, comprising the amino acid sequence APAHRSSTFPKWVTKTERGRQ-PLRS (Seq. ID. No.1) or a fragment thereof, said fragment comprising at least 7 consecutive amino acid residues of Seq. ID. No.1.

3 Claims, 15 Drawing Sheets

APAHRGRGGWTLNSAGYLLLGPVLHLPQMGDQD GKR
ETALEILDLWKAIDGLPYAHPPQPS (SEQ ID NO: 12)

SEQUENCE LISTING

<160> NUMBER OF SEQ ID NOS: 41

<210> SEQ ID NO 1
<211> LENGTH: 25
<212> TYPE: PRT
<213> ORGANISM: Homo sapiens

<400> SEQUENCE: 1

Ala Pro Ala His Arg Ser Ser Thr Phe Pro Lys Trp Val Thr Lys Thr
1               5                   10                  15

Glu Arg Gly Arg Gln Pro Leu Arg Ser
            20                  25

<210> SEQ ID NO 2
<211> LENGTH: 526
<212> TYPE: PRT
<213> ORGANISM: Mycetarotes parallelus

<400> SEQUENCE: 2

Met Ser Thr Asp Asp Trp Arg Glu Asn Ala Lys Arg Pro Ile Arg Arg
1               5                   10                  15

Ala Leu Ile Ser Val Tyr Asp Lys Thr Gly Leu Val Glu Leu Ala Gln
            20                  25                  30

Gly Leu Thr Glu Ala Gly Val Glu Ile Val Ser Thr Gly Ser Thr Ala
        35                  40                  45

Lys Val Ile Ala Glu Lys Gly Ile Pro Val Thr Arg Val Glu Val Leu
    50                  55                  60

Thr Gly Phe Pro Glu Val Leu Asp Gly Arg Val Lys Thr Leu His Pro
65                  70                  75                  80

Arg Val His Ala Gly Leu Leu Ala Asp Leu Arg Lys Pro Glu His Ala
                85                  90                  95

Ala Ala Leu Glu Gln Leu Gly Ile Ala Ala Phe Glu Leu Val Val Val
            100                 105                 110

Asn Leu Tyr Pro Phe Thr Glu Thr Val Asp Ser Gly Ala Gly Ile Asp
        115                 120                 125

Glu Cys Val Glu Gln Ile Asp Ile Gly Gly Pro Ser Met Val Arg Ala
    130                 135                 140

Ala Ala Lys Asn His Pro Ser Val Ala Val Val Val Asp Pro Leu Gly
145                 150                 155                 160

Tyr Asp Gly Val Leu Ala Ala Val Arg His Gly Gly Phe Thr Leu Ala
                165                 170                 175

Glu Arg Lys Arg Leu Ala Ala Leu Ala Phe Gln His Thr Ala Asp Tyr
            180                 185                 190

Asp Ile Ala Val Ala Thr Trp Met Glu Ser Thr Leu Ala Pro Glu His
        195                 200                 205

Pro Pro Thr Thr Phe Pro Lys Trp Leu Gly Arg Ser Arg Arg Ser Ala
    210                 215                 220

Met Leu Arg Tyr Gly Glu Asn Pro His Gln Gln Ala Ser Leu Tyr Ser
225                 230                 235                 240

Asp Pro Gly Ala Trp Pro Gly Leu Ala Gln Ala Glu Gln Leu His Gly
                245                 250                 255

Lys Glu Met Ser Tyr Asn Asn Phe Thr Asp Ala Asp Ala Ala Trp Arg
            260                 265                 270

Ala Ala Phe Asp His Glu Gln Thr Cys Val Ala Ile Ile Lys His Ala
        275                 280                 285

Asn Pro Cys Gly Ile Ala Ile Ser Ser Ile Ser Val Ala Asp Ala His
    290                 295                 300

Arg Lys Ala His Glu Cys Asp Pro Leu Ser Ala Phe Gly Gly Val Ile
305                 310                 315                 320

Ala Ala Asn Thr Glu Val Ser Val Glu Met Ala Glu Tyr Val Ser Thr
                325                 330                 335

Ile Phe Thr Glu Val Ile Ile Ala Pro Ala Tyr Gln Pro Ala Ala Leu
            340                 345                 350

Glu Ile Leu Thr Arg Lys Lys Asn Ile Arg Val Leu Ala Ser Glu
        355                 360                 365

Pro Leu Thr Gly Gly Thr Glu Leu Arg Pro Ile Ser Gly Gly Leu Leu
    370                 375                 380

Val Gln Gln Arg Asp Glu Leu Asp Ala His Gly Asp Asn Pro Ala Asn
385                 390                 395                 400

Trp Thr Leu Ala Thr Gly Ala Pro Ala Asp Pro Ala Thr Leu Ala Asp
                405                 410                 415

Leu Val Phe Ala Trp Arg Val Cys Arg Ala Val Lys Ser Asn Ala Ile
            420                 425                 430

Val Ile Ala Ala Gly Gly Ala Thr Ile Gly Val Gly Met Gly Gln Val
        435                 440                 445

Asn Arg Val Asp Ala Ala Arg Leu Ala Val Glu Arg Gly Gly Asp Arg
    450                 455                 460

Val Arg Gly Ala Val Ala Ala Ser Asp Ala Phe Phe Pro Phe Pro Asp
465                 470                 475                 480

Gly Leu Glu Thr Leu Thr Gly Ala Gly Val Lys Ala Val Val His Pro
                485                 490                 495

Gly Gly Ser Val Arg Asp Asp Glu Val Thr Ala Ala Ala Asn Ala
            500                 505                 510

Gly Ile Thr Leu Tyr Leu Thr Gly Ala Arg His Phe Ala His
        515                 520                 525

<210> SEQ ID NO 3
<211> LENGTH: 166
<212> TYPE: PRT
<213> ORGANISM: Nocardia aerocolonigenes

<400> SEQUENCE: 3

Met Ser Asp Lys Ser Ser Arg Ala Ala Arg Ala Arg Ala His Ala
1               5                   10                  15

Ser Gly Thr Tyr Pro Ala Pro Leu Asn Ala Gly Arg Ser Arg Asn Met
                20                  25                  30

Gln Ala Asn Arg Arg Ser Gly Thr Lys Pro Glu Ala Ala Leu Arg Ser
        35                  40                  45

Ala Leu Phe Lys Leu Gly Tyr Arg Tyr Arg Lys Asp Phe Leu Leu Arg
    50                  55                  60

Leu Gly Asp Gly Val Lys Val Lys Pro Asp Ile Val Phe Thr Ala Arg
65                  70                  75                  80

Lys Val Ala Val Phe Ile Asp Gly Cys Phe Trp His Val Cys Pro Asp
                85                  90                  95

His Gly Arg Gln Pro Thr Thr Asn Glu Trp Tyr Trp Ser Pro Lys Leu
            100                 105                 110

Arg Arg Asn Val Glu Arg Asp Arg Thr Val Asn Gln Ser Leu Thr Asn
        115                 120                 125

Ala Gly Trp Arg Val Leu Arg Val Trp Glu His Glu Glu Leu Gln Asp
    130                 135                 140

Ala Val Ala Ala Val Val Asp Thr Leu His His Leu Glu His Gly Phe
145                 150                 155                 160

Asp Thr Ser Ala Glu Asp
                165

<210> SEQ ID NO 4
<211> LENGTH: 49
<212> TYPE: PRT
<213> ORGANISM: Homo sapiens

<400> SEQUENCE: 4

Met Ala Pro Pro Ser Val Pro Leu Val Leu Leu Val Leu Leu Leu
1               5                   10                  15

Ser Leu Ala Glu Thr Pro Ala Ser Ala Pro Ala His Arg Ser Ser Thr
                20                  25                  30

Phe Pro Lys Trp Val Thr Lys Thr Glu Arg Gly Arg Gln Pro Leu Arg
                35                  40                  45

Ser

<210> SEQ ID NO 5
<211> LENGTH: 116
<212> TYPE: PRT
<213> ORGANISM: Homo sapiens

<400> SEQUENCE: 5

Met Ala Pro Pro Ser Val Pro Leu Val Leu Leu Val Leu Leu Leu
1               5                   10                  15

Ser Leu Ala Glu Thr Pro Ala Ser Ala Pro Ala His Arg Gly Arg Gly
                20                  25                  30

Gly Trp Thr Leu Asn Ser Ala Gly Tyr Leu Leu Gly Pro Val Leu His
                35                  40                  45

Leu Pro Gln Met Gly Asp Gln Asp Gly Lys Arg Glu Thr Ala Leu Glu
        50                  55                  60

Ile Leu Asp Leu Trp Lys Ala Ile Asp Gly Leu Pro Tyr Ser His Pro
65                  70                  75                  80

Pro Gln Pro Ser Lys Arg Asn Val Met Glu Thr Phe Ala Lys Pro Glu
                85                  90                  95

Ile Gly Asp Leu Gly Met Leu Ser Met Lys Ile Pro Lys Glu Glu Asp
                100                 105                 110

Val Leu Lys Ser
        115

<210> SEQ ID NO 6
<211> LENGTH: 115
<212> TYPE: PRT
<213> ORGANISM: Rattus norvegicus

<400> SEQUENCE: 6

Met Ala Cys Ser Lys His Leu Val Leu Phe Leu Thr Ile Leu Leu Ser
1               5                   10                  15

Leu Ala Glu Thr Pro Asp Ser Ala Pro Ala His Arg Gly Arg Gly Gly
                20                  25                  30

Trp Thr Leu Asn Ser Ala Gly Tyr Leu Leu Gly Pro Val Leu His Leu
                35                  40                  45

Ser Ser Lys Ala Asn Gln Gly Arg Lys Thr Asp Ser Ala Leu Glu Ile
        50                  55                  60

Leu Asp Leu Trp Lys Ala Ile Asp Gly Leu Pro Tyr Ser Arg Ser Pro
65                  70                  75                  80

```
Arg Met Thr Lys Arg Ser Met Gly Glu Thr Phe Val Lys Pro Arg Thr
             85                  90                  95

Gly Asp Leu Arg Ile Val Asp Lys Asn Val Pro Asp Glu Glu Ala Thr
            100                 105                 110

Leu Asn Leu
        115
```

<210> SEQ ID NO 7
<211> LENGTH: 120
<212> TYPE: PRT
<213> ORGANISM: Sus scrofa

<400> SEQUENCE: 7

```
Met Ala Leu Thr Val Pro Leu Ile Val Leu Ala Val Leu Leu Ser Leu
1               5                   10                  15

Met Glu Ser Pro Ala Ser Ala Pro Val His Arg Gly Arg Gly Gly Trp
            20                  25                  30

Thr Leu Asn Ser Ala Gly Tyr Leu Leu Gly Pro Val Leu His Pro Pro
        35                  40                  45

Ser Arg Ala Glu Gly Gly Lys Gly Lys Thr Ala Leu Gly Ile Leu
    50                  55                  60

Asp Leu Trp Lys Ala Ile Asp Gly Leu Pro Tyr Pro Gln Ser Gln Leu
65                  70                  75                  80

Ala Ser Lys Arg Ser Leu Gly Glu Thr Phe Ala Lys Pro Asp Ser Gly
                85                  90                  95

Val Thr Phe Val Gly Val Pro Asp Val Val Pro Trp Lys Arg Ile Arg
            100                 105                 110

Pro Gly Thr Thr Arg Phe Gln Ile
        115                 120
```

<210> SEQ ID NO 8
<211> LENGTH: 123
<212> TYPE: PRT
<213> ORGANISM: Homo sapiens

<400> SEQUENCE: 8

```
Met Ala Arg Gly Ser Ala Leu Leu Leu Ala Ser Leu Leu Leu Ala Ala
1               5                   10                  15

Ala Leu Ser Ala Ser Ala Gly Leu Trp Ser Pro Ala Lys Glu Lys Arg
            20                  25                  30

Gly Trp Thr Leu Asn Ser Ala Gly Tyr Leu Leu Gly Pro His Ala Val
        35                  40                  45

Gly Asn His Arg Ser Phe Ser Asp Lys Asn Gly Leu Thr Ser Lys Arg
    50                  55                  60

Glu Leu Arg Pro Glu Asp Asp Met Lys Pro Gly Ser Phe Asp Arg Ser
65                  70                  75                  80

Ile Pro Glu Asn Asn Ile Met Arg Thr Ile Ile Glu Phe Leu Ser Phe
                85                  90                  95

Leu His Leu Lys Glu Ala Gly Ala Leu Asp Arg Leu Leu Asp Leu Pro
            100                 105                 110

Ala Ala Ala Ser Ser Glu Asp Ile Glu Arg Ser
        115                 120
```

<210> SEQ ID NO 9
<211> LENGTH: 25
<212> TYPE: PRT
<213> ORGANISM: Mus musculus

<400> SEQUENCE: 9

```
Ala Pro Ala His Arg Ser Ser Pro Phe Pro Pro Arg Pro Thr Arg Ala
1               5                   10                  15

Gly Arg Glu Thr Gln Leu Leu Arg Ser
            20                  25

<210> SEQ ID NO 10
<211> LENGTH: 25
<212> TYPE: PRT
<213> ORGANISM: Rattus norvegicus

<400> SEQUENCE: 10

Ala Pro Ala His Arg Ser Ser Thr Phe Pro Gln Arg Pro Thr Arg Ala
1               5                   10                  15

Gly Arg Gln Thr Gln Leu Leu Arg Ser
            20                  25

<210> SEQ ID NO 11
<211> LENGTH: 25
<212> TYPE: PRT
<213> ORGANISM: Macaca fascicularis

<400> SEQUENCE: 11

Ala Pro Ala His Gln Ser Ser Thr Phe Pro Lys Trp Val Thr Lys Thr
1               5                   10                  15

Gly Arg Gly Arg Gln Pro Leu Arg Ser
            20                  25

<210> SEQ ID NO 12
<211> LENGTH: 60
<212> TYPE: PRT
<213> ORGANISM: Homo sapiens

<400> SEQUENCE: 12

Ala Pro Ala His Arg Gly Arg Gly Gly Trp Thr Leu Asn Ser Ala Gly
1               5                   10                  15

Tyr Leu Leu Gly Pro Val Leu His Leu Pro Gln Met Gly Asp Gln Asp
            20                  25                  30

Gly Lys Arg Glu Thr Ala Leu Glu Ile Leu Asp Leu Trp Lys Ala Ile
        35                  40                  45

Asp Gly Leu Pro Tyr Ala His Pro Pro Gln Pro Ser
    50                  55                  60

<210> SEQ ID NO 13
<211> LENGTH: 8
<212> TYPE: PRT
<213> ORGANISM: Homo sapiens

<400> SEQUENCE: 13

Arg Ser Ser Thr Phe Pro Lys Trp
1               5

<210> SEQ ID NO 14
<211> LENGTH: 12
<212> TYPE: PRT
<213> ORGANISM: Homo sapiens

<400> SEQUENCE: 14

Ala Pro Ala His Arg Ser Ser Thr Phe Pro Lys Trp
1               5                   10

<210> SEQ ID NO 15
<211> LENGTH: 16
```

```
<212> TYPE: PRT
<213> ORGANISM: Homo sapiens

<400> SEQUENCE: 15

Ala Pro Ala His Arg Ser Ser Thr Phe Pro Lys Trp Val Thr Lys Thr
1               5                   10                  15

<210> SEQ ID NO 16
<211> LENGTH: 21
<212> TYPE: PRT
<213> ORGANISM: Homo sapiens

<400> SEQUENCE: 16

Ala Pro Ala His Arg Ser Ser Thr Phe Pro Lys Trp Val Thr Lys Thr
1               5                   10                  15

Glu Arg Gly Arg Gln
            20

<210> SEQ ID NO 17
<211> LENGTH: 23
<212> TYPE: PRT
<213> ORGANISM: Homo sapiens

<400> SEQUENCE: 17

Ala Pro Ala His Arg Ser Ser Thr Phe Pro Lys Trp Val Thr Lys Thr
1               5                   10                  15

Glu Arg Gly Arg Gln Pro Leu
            20

<210> SEQ ID NO 18
<211> LENGTH: 11
<212> TYPE: PRT
<213> ORGANISM: Homo sapiens

<400> SEQUENCE: 18

Pro Ala His Arg Ser Ser Thr Phe Pro Lys Trp
1               5                   10

<210> SEQ ID NO 19
<211> LENGTH: 10
<212> TYPE: PRT
<213> ORGANISM: Homo sapiens

<400> SEQUENCE: 19

Ala His Arg Ser Ser Thr Phe Pro Lys Trp
1               5                   10

<210> SEQ ID NO 20
<211> LENGTH: 9
<212> TYPE: PRT
<213> ORGANISM: Homo sapiens

<400> SEQUENCE: 20

His Arg Ser Ser Thr Phe Pro Lys Trp
1               5

<210> SEQ ID NO 21
<211> LENGTH: 12
<212> TYPE: PRT
<213> ORGANISM: Homo sapiens

<400> SEQUENCE: 21

His Arg Ser Ser Thr Phe Pro Lys Trp Val Thr Lys
1               5                   10
```

<210> SEQ ID NO 22
<211> LENGTH: 15
<212> TYPE: PRT
<213> ORGANISM: Homo sapiens

<400> SEQUENCE: 22

His Arg Ser Ser Thr Phe Pro Lys Trp Val Thr Lys Thr Glu Arg
1               5                   10                  15

<210> SEQ ID NO 23
<211> LENGTH: 18
<212> TYPE: PRT
<213> ORGANISM: Homo sapiens

<400> SEQUENCE: 23

His Arg Ser Ser Thr Phe Pro Lys Trp Val Thr Lys Thr Glu Arg Gly
1               5                   10                  15

Arg Gln

<210> SEQ ID NO 24
<211> LENGTH: 12
<212> TYPE: PRT
<213> ORGANISM: Homo sapiens

<400> SEQUENCE: 24

Ala His Arg Ser Ser Thr Phe Pro Lys Trp Val Thr
1               5                   10

<210> SEQ ID NO 25
<211> LENGTH: 14
<212> TYPE: PRT
<213> ORGANISM: Homo sapiens

<400> SEQUENCE: 25

Ala His Arg Ser Ser Thr Phe Pro Lys Trp Val Thr Lys Thr
1               5                   10

<210> SEQ ID NO 26
<211> LENGTH: 18
<212> TYPE: PRT
<213> ORGANISM: Homo sapiens

<400> SEQUENCE: 26

Ala His Arg Ser Ser Thr Phe Pro Lys Trp Val Thr Lys Thr Glu Arg
1               5                   10                  15

Gly Arg

<210> SEQ ID NO 27
<211> LENGTH: 21
<212> TYPE: PRT
<213> ORGANISM: Homo sapiens

<400> SEQUENCE: 27

Ala His Arg Ser Ser Thr Phe Pro Lys Trp Val Thr Lys Thr Glu Arg
1               5                   10                  15

Gly Arg Gln Pro Leu
            20

<210> SEQ ID NO 28
<211> LENGTH: 14
<212> TYPE: PRT
<213> ORGANISM: Homo sapiens

<400> SEQUENCE: 28

```
Pro Ala His Arg Ser Ser Thr Phe Pro Lys Trp Val Thr Lys
1               5                   10
```

<210> SEQ ID NO 29
<211> LENGTH: 16
<212> TYPE: PRT
<213> ORGANISM: Homo sapiens

<400> SEQUENCE: 29

```
Pro Ala His Arg Ser Ser Thr Phe Pro Lys Trp Val Thr Lys Thr Glu
1               5                   10                  15
```

<210> SEQ ID NO 30
<211> LENGTH: 17
<212> TYPE: PRT
<213> ORGANISM: Homo sapiens

<400> SEQUENCE: 30

```
Pro Ala His Arg Ser Ser Thr Phe Pro Lys Trp Val Thr Lys Thr Glu
1               5                   10                  15

Arg
```

<210> SEQ ID NO 31
<211> LENGTH: 19
<212> TYPE: PRT
<213> ORGANISM: Homo sapiens

<400> SEQUENCE: 31

```
Pro Ala His Arg Ser Ser Thr Phe Pro Lys Trp Val Thr Lys Thr Glu
1               5                   10                  15

Arg Gly Arg
```

<210> SEQ ID NO 32
<211> LENGTH: 21
<212> TYPE: PRT
<213> ORGANISM: Homo sapiens

<400> SEQUENCE: 32

```
Pro Ala His Arg Ser Ser Thr Phe Pro Lys Trp Val Thr Lys Thr Glu
1               5                   10                  15

Arg Gly Arg Gln Pro
            20
```

<210> SEQ ID NO 33
<211> LENGTH: 23
<212> TYPE: PRT
<213> ORGANISM: Homo sapiens

<400> SEQUENCE: 33

```
Pro Ala His Arg Ser Ser Thr Phe Pro Lys Trp Val Thr Lys Thr Glu
1               5                   10                  15

Arg Gly Arg Gln Pro Leu Arg
            20
```

<210> SEQ ID NO 34
<211> LENGTH: 24
<212> TYPE: PRT
<213> ORGANISM: Homo sapiens

<400> SEQUENCE: 34

```
Pro Ala His Arg Ser Ser Thr Phe Pro Lys Trp Val Thr Lys Thr Glu
1               5                   10                  15
```

Arg Gly Arg Gln Pro Leu Arg Ser
            20

<210> SEQ ID NO 35
<211> LENGTH: 11
<212> TYPE: PRT
<213> ORGANISM: Homo sapiens

<400> SEQUENCE: 35

Ala Ala His Arg Ser Ser Thr Phe Pro Lys Trp
1               5                   10

<210> SEQ ID NO 36
<211> LENGTH: 16
<212> TYPE: PRT
<213> ORGANISM: Homo sapiens

<400> SEQUENCE: 36

Ala Ala His Arg Ser Ser Thr Phe Pro Lys Trp Val Thr Lys Thr Glu
1               5                   10                  15

<210> SEQ ID NO 37
<211> LENGTH: 24
<212> TYPE: PRT
<213> ORGANISM: Homo sapiens

<400> SEQUENCE: 37

Ala Ala His Arg Ser Ser Thr Phe Pro Lys Trp Val Thr Lys Thr Glu
1               5                   10                  15

Arg Gly Arg Gln Pro Leu Arg Ser
            20

<210> SEQ ID NO 38
<211> LENGTH: 20
<212> TYPE: PRT
<213> ORGANISM: Homo sapiens

<400> SEQUENCE: 38

Ala Pro Ala His Arg Ser Ser Thr Phe Pro Lys Trp Arg Gly Arg Gln
1               5                   10                  15

Pro Leu Arg Ser
            20

<210> SEQ ID NO 39
<211> LENGTH: 15
<212> TYPE: PRT
<213> ORGANISM: Homo sapiens

<400> SEQUENCE: 39

Ala Pro Ala His Arg Ser Ser Thr Phe Pro Lys Trp Val Arg Ser
1               5                   10                  15

<210> SEQ ID NO 40
<211> LENGTH: 22
<212> TYPE: PRT
<213> ORGANISM: Homo sapiens

<400> SEQUENCE: 40

Ala Pro Ala His Arg Ser Ser Thr Phe Pro Lys Trp Val Thr Lys Thr
1               5                   10                  15

Glu Gln Pro Leu Arg Ser
            20

<210> SEQ ID NO 41

```
<211> LENGTH: 20
<212> TYPE: PRT
<213> ORGANISM: Homo sapiens

<400> SEQUENCE: 41

Ala Pro Ala His Arg Ser Ser Thr Phe Pro Lys Trp Lys Thr Glu Gln
1               5                   10                  15

Pro Leu Arg Ser
            20
```

NEUROPEPTIDE ALARIN

The present invention relates to novel neuropeptides.

Neuropeptides (NP) are regulatory peptides with a widespread occurrence through evolution. They are primarily produced in the central nervous system. Most NP are also synthesised and act in nonneuronal tissues such as the endocrine system. Whereas some NP appear to be restricted to the central nervous system others are more widely distributed in various regions of the body, especially mucosal cells in the gastrointestinal tract, the pancreas, adrenal medulla, gonads, placenta and peripheral nerves and ganglia.

It has become increasingly clear that one of the most important functions of NPs is the integration of the functions of the brain and the systems of the body. The list of functions in which NP are involved is long and includes regulation of reproduction, growth, water and salt metabolism, temperature control, food and water intake, cardiovascular, gastrointestinal and respiratory control, behaviour and memory. They also affect nerve development and regeneration. These features and the large number of NP and NP receptors provide many opportunities for the discovery of new drug targets for the treatment of nervous system disorders.

NP are derived from large precursor molecules. These precursors sometimes code for more than one NP. It was suggested, half humorously, that there are four basic rules for peptide evolution:

1.: Conserve the biological important part of the molecule—one can play around with the rest: the structure of NP has strongly been conserved throughout evolution, for example, the first 15 amino acids of NP galanin are fully conserved from fish to humans because this part of the peptide is essential for receptor binding.
2.: Never make a new peptide if you can use an old one: the economy of evolutionary development has resulted in the retention of the chemical structure of many NP even as their functions and receptors have changed. For galanin three receptor subtypes are known which couple to different second messenger systems depending on the expression in specific cells.
3.: Everything is made everywhere: one of the first attempts to classify NP was based on their source, for example hypothalamus and pituitary. Because of the diversity of tissues expressing NP now a major functional classification is used; Galanin initially isolated form porcine intestine by Tatemoto et al., 1983 has now been shown to be widely distributed throughout the central and peripheral nervous system as well as in non neuronal cells.
4.: Gene duplication is the name of the game: the existence of families of NP indicates that they were generated through successive events of gene duplication within a common ancestral peptide. This process fries on part of the genome from selective pressure and permits a small error rate of mutation; Galanin-like-peptide (GALP) a 60 amino acid peptide shares 13 amino acids with galanin (1-13) which are important for the binding of the peptide to the galanin receptor type 2 (GalR2; Ohtaki et al., 1999, EP 1 360 964 A1).

The analysis of alternative splicing has attracted interest, as the number of expressed proteins is substantially larger than the number of genes encoded in the human genome. Alternative posttranscriptional splicing is an important mechanism for increasing the potential number of gene products. It has been estimated to occur in 35% of human genes. The resulting proteomic diversity is particularly important in the nervous system, where the peptide/protein isoforms play roles in complex processes such as learning and memory as well as neurotransmission. In addition to the rules for NP diversity mentioned above and the possibility that several NP can be processed from one large precursor molecule also differential splicing is employed to generate different NP from one gene. For example the calcitonin gene related peptide (CGRP) gene is alternately spliced to produce calcitonin, a hormone involved in calcium homeostasis in non-neuronal cells, and CGRP a potent vasodilator NP in neural cells. Calcitonin mRNA is produced by splicing of exons 1, 2, 3 and 4 and CGRP is made of exon 1, 2, 3, 5 and 6. This regulation is executed by neural specific inhibition of splicing to exon 4, which encodes calcitonin. The prepro-tachykinin (PPT-A) gene encodes several tachykinin peptides (Substance P, neurokinin A, neuropeptide P and neuropeptide K) with distinct pharmacological properties. The mechanisms accounting for the expression of several tachykinins from the PPT-A gene include alternative posttranscriptional splicing and posttranslational processing. The differential expression of splice variants of a gene may occur in distinct tissues and organs, may be regulated developmentally or may vary within one tissue type.

For the galanin system only for avian and goldfish galanin mRNA differential splicing has been described (Kohchi et al., 2000). However, the physiological significance of these multiple forms of galanin mRNA in these organisms is unknown. No splice variants for GALP have been reported to date.

Neuropeptide Galanin (GAL) is a 29-30-amino acid peptide, initially isolated from porcine intestine in 1983. Subsequently, it has been shown to have a widespread distribution in the central and peripheral nervous systems of many mammalian species. Consistent with its widespread distribution, physiological studies in a number of animal model systems and in man have allowed identification of a diversity of biological effects, some of which are species-specific. These include effects on the secretion of hormones such as insulin, glucagon, and growth hormone, effects on neurotransmitter release in the hippocampus, inhibition of memory and learning, central and peripheral effects on the cardiovascular system, stimulation of appetite, inhibition of sexual activity, analgesic effects in response to nerve injury, and mitogenic effects on developing brain tissue and small cell lung cancer cell lines.

Molecular cloning has revealed the existence of at least three human galanin receptor subtypes GalR1, GalR2 and GalR3 (Floren et al., 2000). Galanin receptors belong to the G protein-coupled receptor super family. Galanin receptors have been found in several sensory systems, in gastric smooth muscle, hypothalamus, mucosal epithelial cells lining the gastrointestinal tract and human ocular ciliary epithelium. In addition, galanin receptors are expressed in neuroblastomas, pancreatic cell lines, the human Bowes melanoma cell line and neuronal structures of human dermis.

Galanin-like peptide (GALP) was originally discovered as an endogenous ligand of galanin receptors in the porcine hypothalamus. GALP (9-21) is identical to galanin (1-13) and the sequence homology among the species is high. The human GALP gene is located on chromosome 19q13.43 and is comprised of six exons (Cunningham et al., 2002). GALP mRNA has since been found in several other mammalian species. In the rat brain, GALP mRNA and protein have been found in cell bodies residing exclusively in the hypothalamic arcuate nucleus and median eminence, and this distribution is conserved across all species studied to date. GALP immunoreactive fibres project to various regions of the forebrain, including the lateral septum, bed nucleus of the stria terminalis, medial preoptic area and the parvicellular region of the paraventricular hypothalamic nucleus. Currently, no reports are available concerning the cellular expression of GALP mRNA or peptide in different human tissues.

GALP has been implicated in both the homeostatic regulation of feeding and body weight, as well as the control of the hypothalamic-pituitary-gonadal axis. The expression of GALP mRNA is up regulated by leptin injections in both fasted rats and leptin-deficient ob/ob mice. Intracerebroventricular (i.c.v.) injections of GALP alter food intake and body weight in both rats and mice in a time-dependent manner. Similarly, these rodent species exhibit a release of luteinising hormone (LH) and testosterone after i.c.v. injection of GALP, which is attributable to its stimulatory effects on gonadotropin-releasing hormone (GnRH) neurones.

In the macaque Cunningham et al. have recently shown that GALP neurons play a role of integrating metabolic signals which are related to circuits controlling GnRH release.

An object of the present invention is to provide for novel neuropeptides, especially different splice variants of known neuropeptides.

Therefore, the present invention relates to a polypeptide, comprising the amino acid sequence APAHRSSTFPKWVTKTERGRQPLRS (Seq. ID. No.1), hereinafter also referred to as "alarin" or a fragment thereof, said fragment comprising at least 7 consecutive amino acid residues of Seq. ID. No.1. Amino acid residues are indicated in the single letter code of the usual amino acids (i.e. A is alanine, P is proline, etc.).

Preferred fragments comprise amino acid residues 2-24, preferably 3-20, especially 3-15 of Seq. ID. No.1. Other preferred fragments are 1 to 10, 1 to 12, 1 to 14, 1 to 16, 1 to 18, and 1 to 20, 3 to 10, 3 to 12, 3 to 14, 3 to 16, 3 to 18, and 3 to 20, 5 to 12, 5 to 14, 5 to 16, 5 to 18, 5 to 20 and 5 to 22, 7 to 14, 7 to 16, 7 to 18, 7 to 20 and 7 to 22, 9 to 16, 9 to 18, 9 to 20, 9 to 22 and 9 to 25, 11 to 18, 11 to 20, 11 to 22 and 11 to 25, 11 to 20, 11 to 22 and 11 to 25, 13 to 22 and 13 to 25 and 15 to 25 of Seq. ID. No.1 or homologues of other mammals, such as mouse, rat or macacqe. Such fragments are specifically useful for diagnostic and scientific markers allowing a specific identifcation of alarin or addressing alarin specific questions.

Preferred alarin fragments can have the following sequence:

```
APAHRSSTFPKW,                (SEQ ID NO: 14)
APAHRSSTFPKWVTKT,            (SEQ ID NO: 15)
APAHRSSTFPKWVTKTERGRQ,       (SEQ ID NO: 16)
APAHRSSTFPKWVTKTERGRQPL,     (SEQ ID NO: 17)
PAHRSSTFPKW,                 (SEQ ID NO: 18)
AHRSSTFPKW,                  (SEQ ID NO: 19)
HRSSTFPKW,                   (SEQ ID NO: 20)
HRSSTFPKWVTK,                (SEQ ID NO: 21)
HRSSTFPKWVTKTER,             (SEQ ID NO: 22)
HRSSTFPKWVTKTERGRQ,          (SEQ ID NO: 23)
AHRSSTFPKWVT,                (SEQ ID NO: 24)
AHRSSTFPKWVTKT,              (SEQ ID NO: 25)
AHRSSTFPKWVTKTERGR,          (SEQ ID NO: 26)
AHRSSTFPKWVTKTERGRQPL,       (SEQ ID NO: 27)
```

-continued
```
PAHRSSTFPKWVTK,              (SEQ ID NO: 28)
PAHRSSTFPKWVTKTE,            (SEQ ID NO: 29)
PAHRSSTFPKWVTKTER,           (SEQ ID NO: 30)
PAHRSSTFPKWVTKTERGR,         (SEQ ID NO: 31)
PAHRSSTFPKWVTKTERGRQP,       (SEQ ID NO: 32)
PAHRSSTFPKWVTKTERGRQPLR,     (SEQ ID NO: 33)
PAHRSSTFPKWVTKTERGRQPLRS,    (SEQ ID NO: 34)
AAHRSSTFPKW,                 (SEQ ID NO: 35)
AAHRSSTFPKWVTKTE,            (SEQ ID NO: 36)
AAHRSSTFPKWVTKTERGRQPLRS,    (SEQ ID NO: 37)
APAHRSSTFPKWRGRQPLRS,        (SEQ ID NO: 38)
APAHRSSTFPKWVRS,             (SEQ ID NO: 39)
APAHRSSTFPKWVTKTEQPLRS       (SEQ ID NO: 40)
or
APAHRSSTFPKWKTEQPLRS.        (SEQ ID NO: 41)
```

The polypeptide according to the present invention (e.g. polypeptides consisting of amino acid residues 1 to 25 of Seq. ID. No. 1 or the preferred fragments) may also further comprise an additional N-terminal and/or C-terminal polypeptide sequence or chemical modification(s). In WO 2004/094589 A2 a nucleic acid has been identified in a screening process for secretory proteins encoding an N-terminal extension with the sequence MAPPSVPLVLLLVLLLSLAETPAS (referred to as "Seq. ID. No. 5" in this document). No function and therefore no technical information was provided for this sequence. Preferably and only if necessary, this very sequence may also be regarded as being excluded as such from the present invention as far as the subject matter of the peptides as such is concerned. This does, of course, not relate to the specific uses of the present invention. Also alanin mimicks can easily provided by the skilled man in the art, e.g. by testing peptide libraries or other chemical libraries with an alanin antibody or an alanin receptor or alanin itself for binding.

The present invention also relates to alarin homologues from other animals. Counterparts of galanin and GALP have been identified and isolated in many animals, such as mouse, rat, macacqe, etc. Also the alarin according to the present invention has such a counterpart. Sequences of the homologues are highly homologous (80% amino acid identity or more) between various mammal species, especially in the first part of the peptide (first 10 amino acids); in the rest of the peptide (11 to 20 amino acid residues) 80% or more identity is given between related species. The present invention also relates to structurally and/or functionally active homologue alarin molecules of other mammal species. Preferably, these alarin homologues have an amino acid identity degree to the human, mouse, rat or macacqe of at least 80%, especially of at least 90%. Specifically preferred alarin molecules are molecules with 20 to 30, especially 22 to 27 amino acid residues which have at least 80% amino acid identity to amino acid residues 1 to 10 of human, mouse, rat or macacqe alarin and have either alarin activity or are bound by an antibody specifically recognising human, mouse, rat or macacqe alarin, respectively.

According to a preferred embodiment, the polypeptide according to the present invention is a fusion protein of said amino acid sequence according to Seq. ID. No. 1 or said fragment thereof and a carrier protein. This carrier protein is preferably a marker protein, an immunogenic protein, a selection protein, a transport protein or a protection protein.

According to another aspect, the present invention also relates to a method for the detection of cells expressing a polypeptide according to the present invention, characterised by the following steps:
  providing a cell sample, tissue sample or a sample of a cell or tissue extract,
  contacting said sample with a detection molecule being specific for an alarin polypeptide according to the present invention or for a nucleic acid encoding said polypeptide, wherein said detection molecule is allowed to bind to said polypeptide or nucleic acid encoding said polypeptide, and
  analysation of the binding of the detection molecule to the polypeptide or nucleic acid encoding said polypeptide.

Preferably, the detection molecule is an antibody, a nucleic acid or a receptor.

According to a preferred embodiment, the detection molecule comprises a tag, especially an antigen tag, a colorigenic tag, a fluorogenic tag, a metal ion tag, a radioactive tag or combinations thereof.

The present invention also relates to an antibody being specific against a polypeptide according to the present invention, wherein said specificity is defined by a lack of crossreactivity to galanin and galanin-like peptide.

Furthermore, the present invention relates to a method for the detection and optionally isolation of a receptor for the polypeptide according to Seq. ID. No. 1, said method being characterised by the following steps:
  providing a sample with a receptor candidate,
  providing a polypeptide according to Seq. ID. No. 1, optionally combined with a detection marker,
  mixing said sample with said polypeptide, wherein the polypeptide is allowed to contact the receptor candidate and
  assessing whether a binding event between the receptor candidate and the polypeptide is taking place, said binding event identifying a receptor, and, optionally, isolating said receptor.

Moreover, the present invention relates to a method for activation of a receptor for the polypeptides according to Seq. ID. No.1, said method being characterised by the following steps:
  providing a sample with a receptor candidate,
  providing a polypeptide according to Seq. ID. No. 1, optionally combined with a detection marker,
  mixing said sample with said polypeptide, wherein the polypeptide is allowed to contact the receptor candidate and
  assessing whether a binding event between the receptor candidate and the polypeptide is taking place, said binding event identifying a cellular response upon receptor activation.

Preferably, the method for producing an antibody against a polypeptide according to the present invention is characterised in that a polypeptide according to the present invention is applied to an animal so that said animal produces antibodies against said polypeptide and recovering antibodies being specific for said polypeptide from said animal.

Alternatively, an antibody against a polypeptide according to the present invention may be produced by a method comprising the the following steps:

applying a polypeptide according to the present invention to an animal so that said animal produces antibodies against said polypeptide,
  removing spleen cells from said animal,
  fusing said spleen cells with a cell line being capable of forming antibody producing hybridoma cells when fused to said spleen cells,
  isolating hybridoma cells specific for the polypeptide according to the present invention,
  cultivating said specific hybridoma cells thereby producing monoclonal antibodies against said polypeptide and isolating said monoclonal antibodies.

Various diseases can be investigated whether alarin gene expression is specifically deregulated in certain diseases or disorders. Specifically preferred are certain types of tumors, especially tumors of neuronal origin. Alarin is then employed as specific tumor marker for neuroblastoma and pheochromocytoma (somastation szintigrahy is applied for neuroblastoma and pheochromocytoma). Alarin expression in the gut can be monitored for assessment of the regulation of motility and secretion of the gastrointestinal tract. Alarin expression around blood vessels may be used e.g. for assessment of the regulation of blood pressure. Alarin expression in the brain can be used for monitoring stress, appetite, memory or learning, especially hypothalamus-pituitory regulation of the neuroendocrine system. Deregulation of alarin expression may be assessed in tissue or body fluid samples of Alzheimer, Parkinson, epileptic patients and the like. Alarin expression can be monitored in the peripheral nervous system, especially in patients with neuroinflammatory disorders or pain.

The present invention therefore relates to alarin detection methods wherein alarin or alarin mRNA is detected in samples, especially body fluids or tissue samples. Alarin (or alarin mRNA) detection may be performed by any method suitable, especially alarin detection by alarin specific antibodies (i.e. antibodies recognising alarin but not GALP), e.g. in an ELISA, mass spectroscopy, mRNA detection by PCR or other nucleic acid amplification methods with alarin specific primers and/or probes (i.e. specific for alarin, but not for GALP), detection of alarin splice variants, etection by exon-specific probes, etc.

The present invention also relates to the identification of differentiated tumor cells in neuroblastomas, because alarin expression, especially detected as alarin-like immunoreactivity or alarin specific mRNA is specific for ganglioneuroma or ganglioneuroblastoma as well as differentiated tumor cells of neuroblastoma tissues. Alarin specific antibodies are preferably used as tumor marker to further define the prognosis of patients with neuroblastic tumors.

The presence of alarin in the pituitary allows the detection of alarin by alarin antibodies in plasma or tumor tissues of patients with pituitary hyperplasia's as a marker with diagnostic and prognostic value.

Moreover, the skin has an essential protective function in responding to challenges from the environment. Neuropeptides such as alarin contribute to the physiological and pathophysiological modulation of skin responses. Several neuropeptides are invovled in wound healing and therefore the polypeptides according to the present invention are used for improvement of wound healing.

Brain-body(skin) influences are bi-directional and skin can be considered as an active neuro-immuno-endocrine interface, where effector molecules act as common words used in a dynamic dialogue between brain, immune-system and skin. It has been widely demonstrated that stimuli received in the skin can influence the immune, endocrine and nervous systems at both a local and central level. However, the brain can also modulate inflammatory conditions locally induced in the skin. The skin can therefore alter the pharmacology of the CNS by releasing large amounts of NPs which obviously do work locally in the skin and beyond the skin. Alarin may represent a key molecule for understanding this aspect of cutaneous-immune-neuro-endocrine-mental biological communication, being it is also generated in the skin. Therefore, the polypeptides according to the present invention are used for the manufacture of potent anti-inflammatory agents in clinical dermatology.

Since corneal nerves are frequently subjected to injury due to refractive surgery, chemical trauma, inflammation or infectious corneal diseases, many compounds expressed in the cornea like alarin have the potential to enhance or to regulate neural recovery. They have a major clinical significance in terms of improving of wound healing, management of ocular surface disease related to neurotrophic keratitis or elimination of chronic corneal pain, which relatively frequently occurs after e.g. ophthalmic zoster, and sometimes even after corneal surgery. Thus, assessment of the status of the corneal nerves e.g. by alarin antibodies, the basis for diagnosis of certain corneal diseases, is a very valuable parameter. This use of alarin antibodies is therefore another aspect of the present invention.

The polypeptides according to the present invention, especially topically applied neuropeptides and neurotrophins may be used for the manufacture of a medicament to treat neurotrophic keratitis.

Alarin and the other polypeptides according to the present invention may be used for the manucfacture of therapeutic agents to cure retinal diseases. This is further strengthened by clinical trials with neuropeptide analogs of somatostatin to treat diabetic retinopathy, a retinal disease with high social impact and originating as a complication of diabetes (*stol Histopathol.* 2005 April; 20(2):615-32).

Immune cells express and release numerous neuropeptides. Some of these neuropeptides are released in functionally relevant amounts during the immune response, both in patients and in animal models. For example substance P is released from neutrophils in inflamed regions, and thus, substance P may modulate clinical inflammatory response by release from either neuronal or immunocompetent cell populations (*J Endod.* 2004 May; 30(5) :329-32).

Expression of alarin in neutrophils shows also a role of the peptide in inflammation and host defense of pathogens (innate immunity). Therefore, the polypeptides according to the present invention are used for the manufacure of a medicament for treating acute and chronic inflammatory and autoimmune diseases, such as septic shock, arthritis, multiple sclerosis, Cohn's disease, or autoimmune diabetes.

The pituitary hypothalamic axis regulates the release of ACTH, TSH, LH, prolactin (PRL) and GH. Adrenocorticotropin hormone (ACTH) is a product of the hypothalamus-pituitary adrenal axis (HPAA) which stimulates secretion of corticosteroids from adrenals. In turn, corticosteroids modulate the immune response in virtue of their anti-inflammatory activity.

The significant influence of CNS injections of alarin on food intake, body weight and pituitary hormone secretion shows an important role in the physiological control of metabolism and reproduction. Therapeutic potential in regulating pituitary function is based on the presence of alarin in the pituitary. These functions include regulation of appetite and body weight as well as reproduction, growth. As also shown by the present functional studies the polypeptides according to the present invention are used for the manufacture of a medicament for treatment of obesity, growth deficits, ect.

Obesity is increasing at an alarming rate in industrialized and developing countries alike and is associated with a wealth of conditions afflicting virtually all organ systems. Examples diverge widely to include cholelithiasis, osteoarthritis, infertility, stroke, cutaneous infections, wound healing deficiencies, as well as a general increase in mortality and social and professional stigmatization. Several novel compounds are now being tested in clinical trials, phases II and III. Many of these compounds target neuropeptide systems. The selective neuroanatomical distribution of many neuropeptides may provide an advantage in attempting to minimize side-effects (J Intern Med. 2005 October; 258(4):301-27).

Therefore, the molecules of the present invention as alarin agonists (especially the specific antibodies) may also be of clinical use to treat obesity and—on the other hand—the polypeptides according to the present invention as alarin antagonists to treat anorexia.

Regulation of LH levels is important for gynecologic disorders, polycystic ovary disease (PCOD), in vitro fertilization-embryo transfer (IVF-ET), benign prostatic hypertrophy (BPH), precocious puberty and contraception. Since alarin is able to induce LH secretion alarin antagonists (e.g. the antibodies according to the present invention) inhibit LH secretion immediately after their administration and thus achieve rapid therapeutic effects. Alarin antagonists have applications in the treatment of uterine leiomyomas, endometriosis, and in controlled ovarian stimulation-assisted reproductive techniques.

All methods described above may be carried out with the polypeptide according to Seq. ID No. 1. or any other fragment, derivative or homologue of alarin.

The present invention is further illustrated by the following examples and the drawing figures, yet without being restricted thereto.

Figures

FIG. 1 shows that differential splicing of the GALP mRNA (A) leads to a frame shift creating the novel peptide alarin (B,C). A: RT-PCR using primers spanning exon 2 to 5 of human GALP mRNA; M: 100 bp ladder, lane 1: negative control, lane 2: neuroblastoma cell line SY5Y, lanes 3-7 neuroblastoma tissues, lane 8: ganglioneuroma. B: Sequence of lower PCR product; C: schematic drawing of GALP spice variants: blue boxes are identical amino acids in GALP and alarin. Red/white box indicate the homology of GALP with galanin. Numbers indicate the amino acid positions of the precursor peptides.

FIG. 2: shows IH of a ganglioneuroma tissue (stage 1, female, 2 years); A,B, D-H stained: with a affinity purified alarin polyclonal antiserum (1:100); C with an alarin pre-immunserum (1:100); B,D,E,F,H antiserum pre-absorbed with a synthetic peptide as indicated. A-F: cryostat sections; G,H: paraffin tissue of same patient showing more intense staining at the plasma membrane of ganglia.

F*ig*.3: IF/IH staining and RT-PCR of cryostat sections of ganglioneuroma and neuroblastom tissues with affinity purified alarin (6-25) antiserum (1:100). A,B: IF of ganglioneuroma tissue (stage 1, female, 2 years) and C: RT-PCR of consecutive sections. E,F: IH of neuroblastoma tissue (NB 19: stage 4, 17 years, female) and G: RT-PCR of consecutive sections. H,I: Alarin-LI in blood vessels (bv) of neuroblastoma tissue (NB: 11 stage male, 18 months). Negative control: water; positive control: RNA isolated of human neuroblastoma cell line SMS-KAN.

FIG. 4: A,B IH of a human rectum biopsy (male, 5 years) stained A,C: with affinity purified alarin polyclonal antiserum; B,C with alarin antiserum pre-absorbed with a synthetic alarin peptide. C,D: IH paraffin embedded cortex tissue (adult, male).

FIG. 5 shows an amino acid sequence of mature human GALP. The homology to alarin is indicated by blue letters, the homology to galanin in green. The arrow indicates a potential proteolytic cleavage site. The sequences of the synthetic peptides which could be used for production of antibodies are underlined.

FIG. 6 shows an alignment of an alarin peptide, alarin, and some GALP and Galanin sequences.

Figure 8:
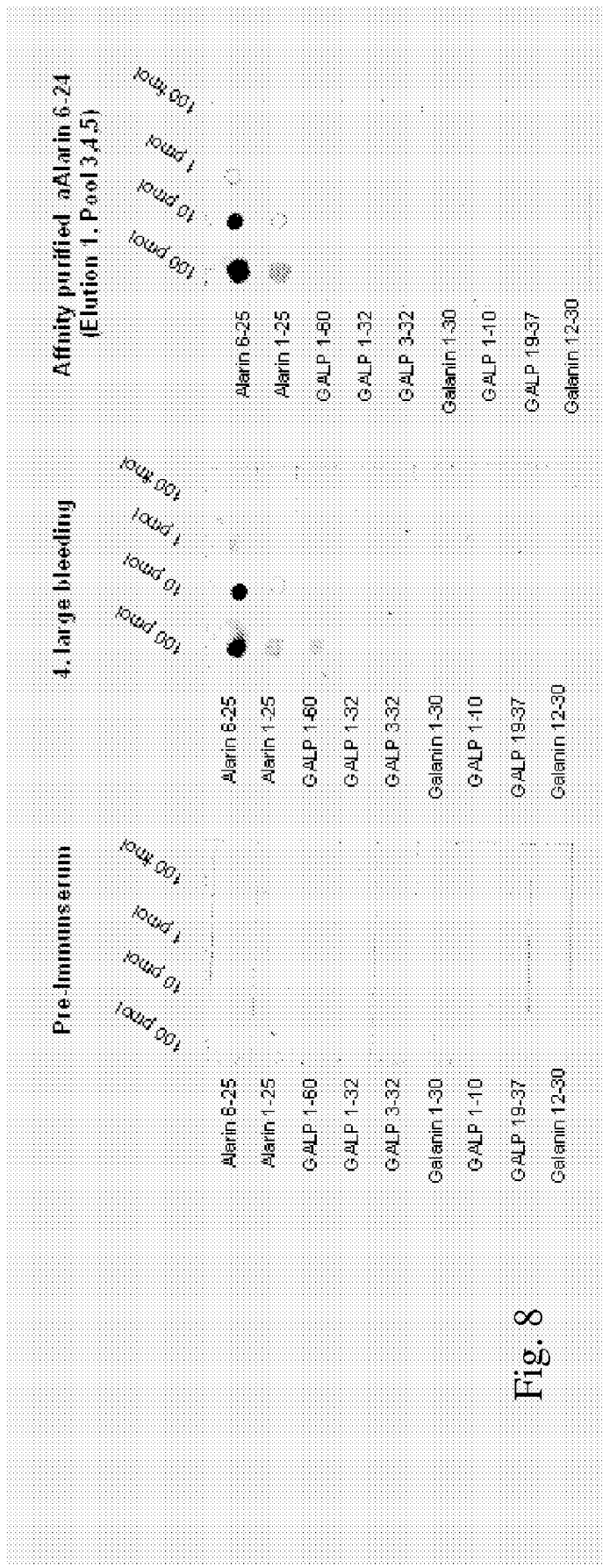
Figure 9:
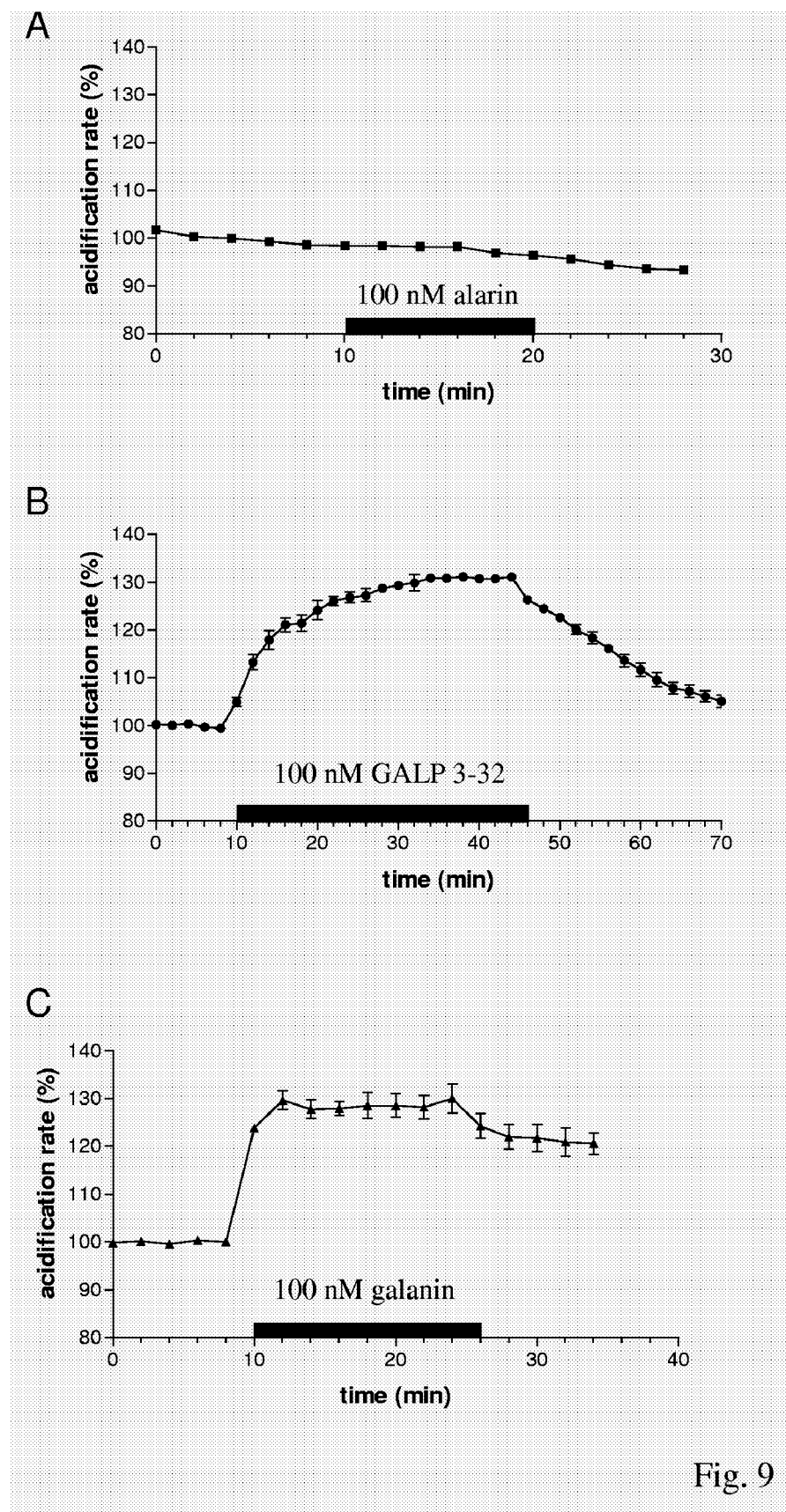

FIG. 8 shows dot blot analysis of specificity of human alarin (6-25) anti serum. Incubation with (1:200) dilution of serum or affinity purified alarin antiserum. Affinity purification was carried out using an alarin 6-25 affinity column. After affinity purification the weak crossreactivity of the polyclonal antiserum with GALP-1-60 is eliminated FIG. 9 shows microphysiometry using human neuroblastoma cells SY5Y expressing GALR2 receptor. No change in extracelluar acidification upon treatment with alarin (100 nM; A) in contrast to a 20-30% increase in extracellular acidification upon treatment with the known galanin receptor R2 ligands galanin (C) and GALP (B).

Figure 10:
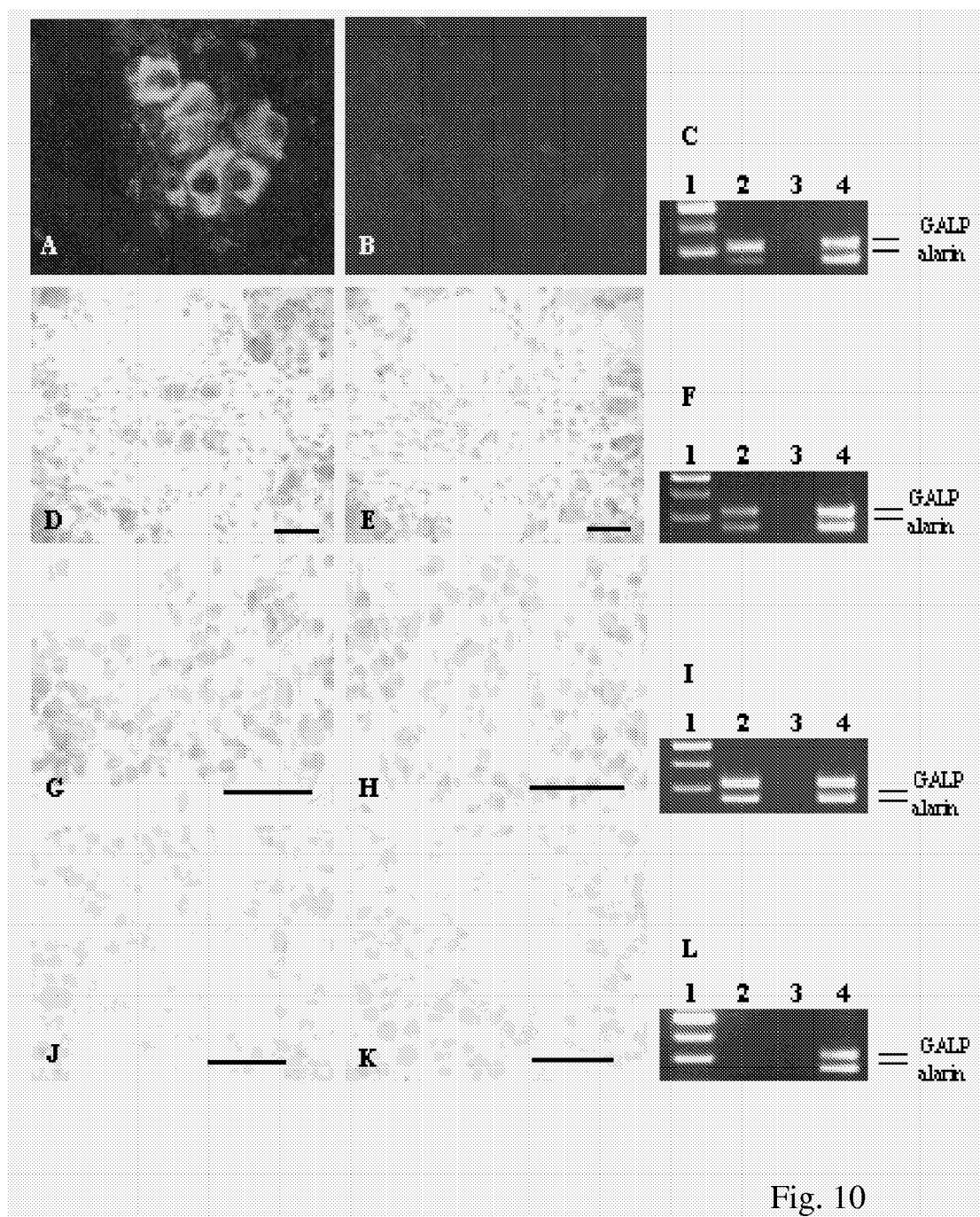

FIG. 10 shows alarin-LI staining and RT-PCR of cryostat sections of ganglioneuroma (4 years, female, stage 1; A,B,C), ganglioneuroblastoma (13 months, male, stage 3; D,E,F), differentiated neuroblastoma (6 years, male, stage 3; G,H,I) and undifferentiated neuroblastoma (17 years, female, stage 4; J,K,L). (A,D,G,J) staining with affinity purified alarin (6-24) antiserum (1:200), (B,E,H,K) staining preabsorbed with 3 μM synthetic alarin 6-24-Cys peptide. (C,F,I,L) RT-PCR of consecutive sections with GALP primers spanning exon 2 to 5; lane 1: 100 bp ladder, lane 2: respective tumor tissues, lane 3: negative control, lane 4: positive control, human basal ganglia. Scale bar=50 μm.

Figure 11:
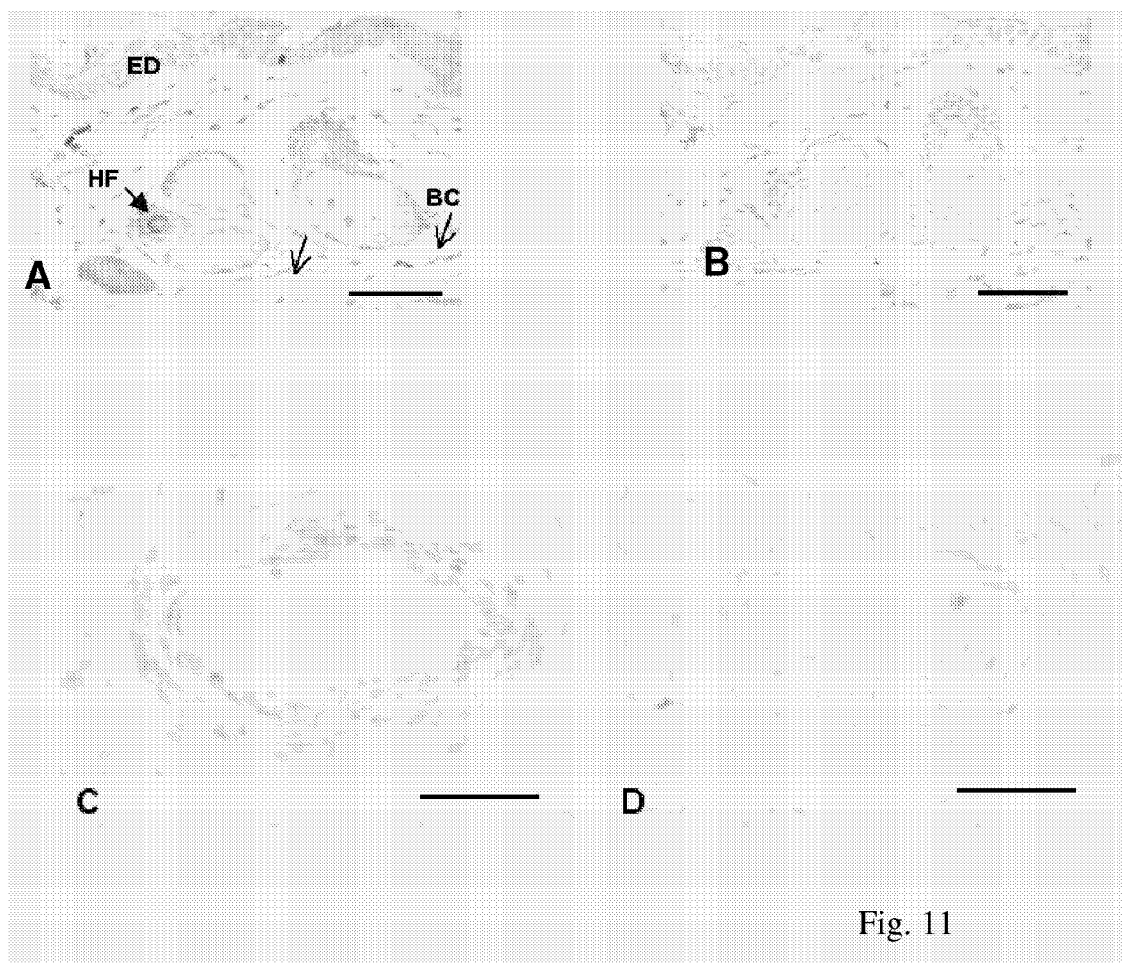

FIG. 11 shows alarin staining in murine skin (A). Alarin staining performed with a preabsorbed antibody (B). ED: epidermis, HF: hair follicle; BC: dermal blood capillary scale bar 50 μm. Alarin staining in smooth muscle cells around a human blood vessel (C, D) staining performed with a preabsorbed antibody. scale bar 50 μm.

Figure 12:
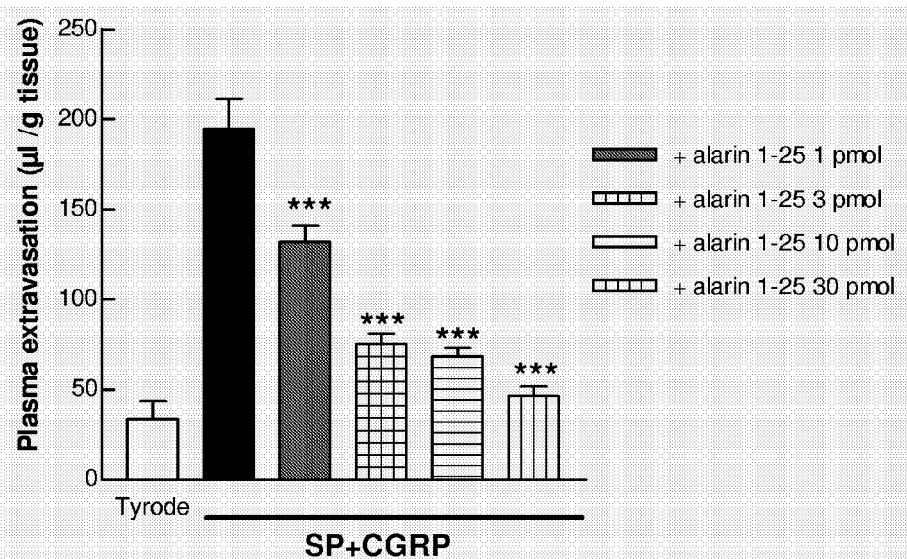

FIG. 12 shows the effect on oedema formation in CD-1 mouse skin. Inflammatory oedema was induced in response to intradermally injected SP (300 pmol) with CGRP (10 pmol). ***P<0.001

Figure 13:
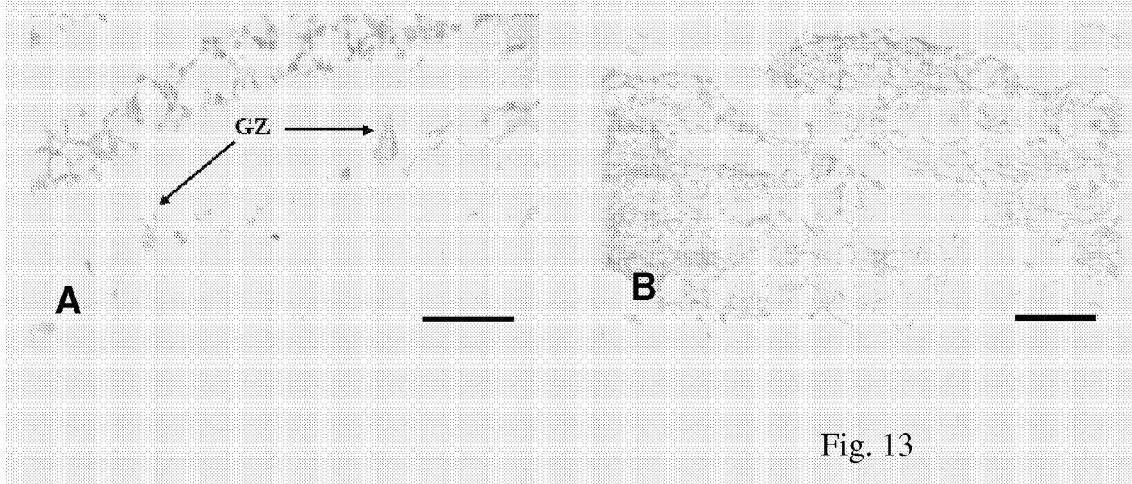

FIG. 13 shows alarin staining in human eye (A, B). A: Ganglionic cell (GZ) in retina; B: optical nerve. scale bar 50 μm.

Figure 14:
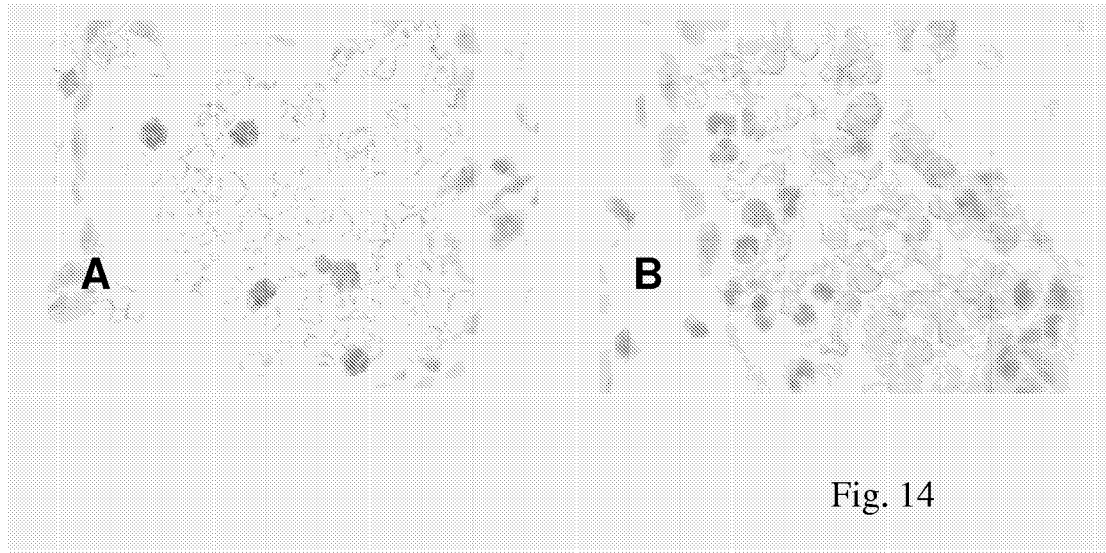

FIG. 14 shows alarin staining of human blood cells present in a blood vessel of a ganglioneuroma tissue (A). Staining performed with a preabsorbed antibody (B). Brown staining indicates alarin-like immunoreactivity in neutrophils.

Figure 15:
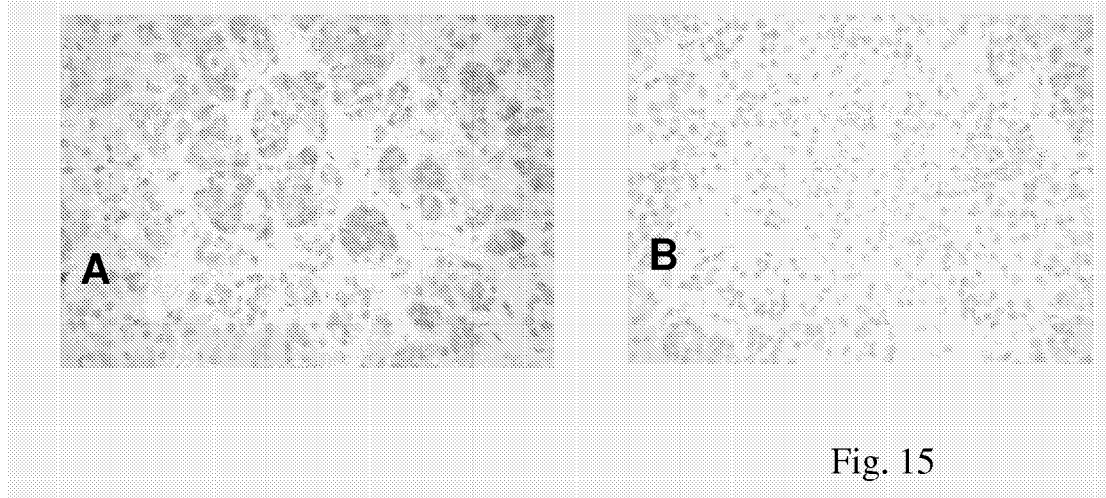

FIG. 15 shows alarin staining in human pituitary (A). Staining performed with a preabsorbed antibody (B). Green staining indicates alarin-like immunoreactivity.

Figure 16:
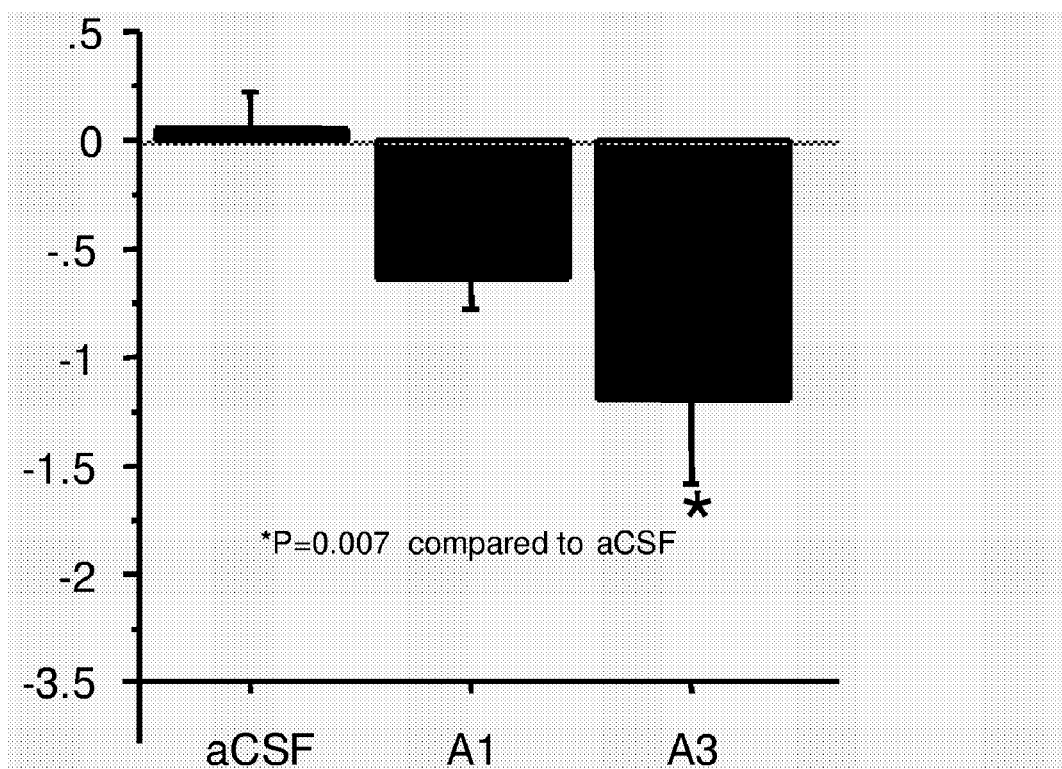

FIG. 16 shows intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Body weight was measured at 1 hr post injection. (Shown here as percent change in body weight from baseline).

Figure 17:
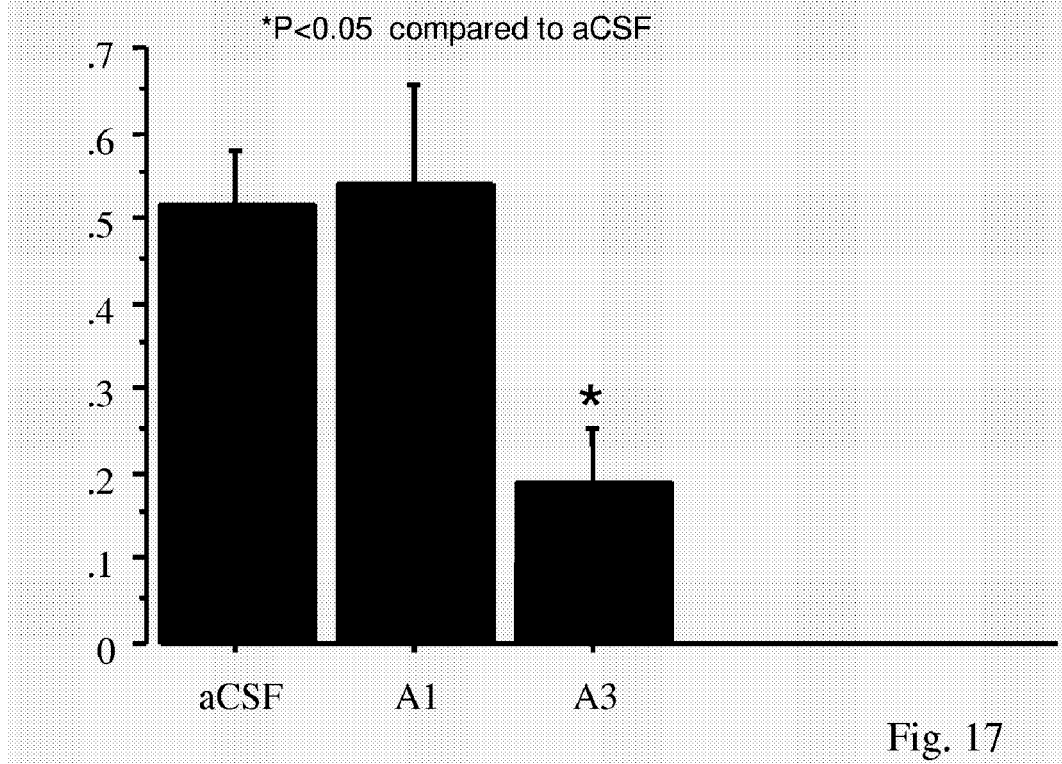

FIG. 17 shows intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Food intake was measured at 1 hr post injection. (Shown here as percent change in body weight from baseline).

Figure 18:
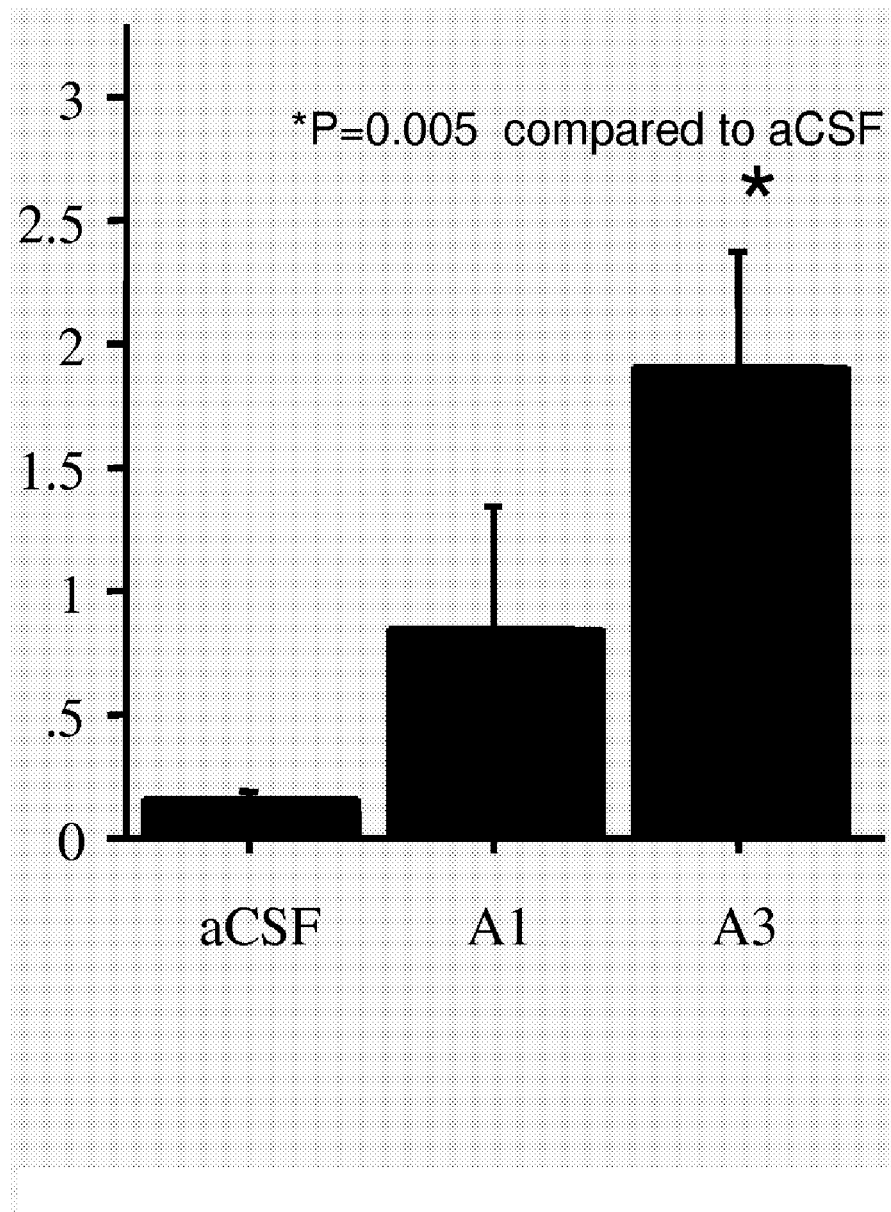

FIG. 18 shows intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Blood was collected 30 min after injection and serum was assayed for LH content. (LH levels shown here in ng/ml).

EXAMPLES

Analysis of mRNA Expression Levels

Figure 1:
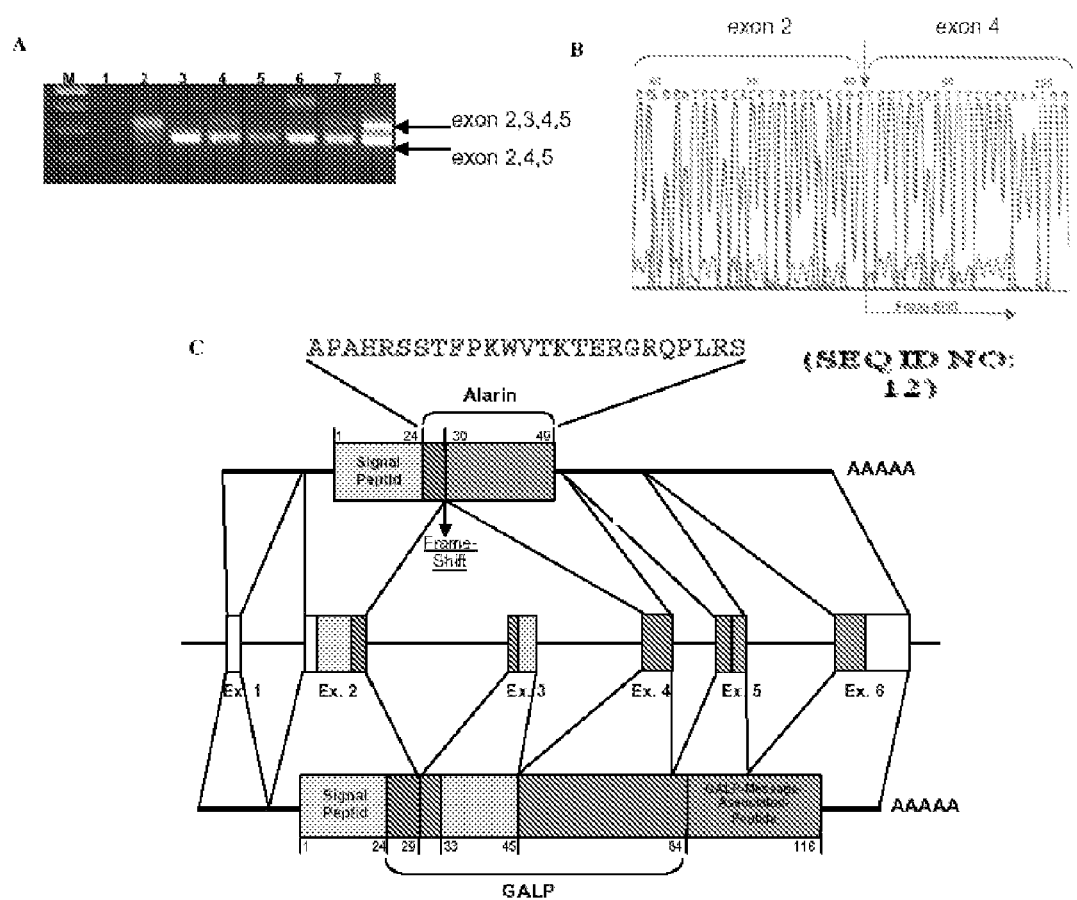

Quantitative real time RT-PCR with alarin and GALP specific primers/probes are be used to detect the level of differential splicing of the GALP gene. Different cell lines and tissues are to be analysed to detect the level of production of alarin mRNA (Fig IF/IH staining and RT-PCR of cryostat sections, FIG. 1). In addition, murine, rat and macaque RNA samples form different tissues and are tested by RT-PCR for the expression of the alarin splice variant.

Analysis of the Full Length Alarin mRNA

A 5' RACE System is suitable for rapid amplification of cDNA ends (RACE; Gene Racer Kit: Invitrogen). The system is useful for capturing the 5' end information of mRNA. First strand cDNA synthesis is initiated from an alarin specific primer. An oligo dC anchor sequence is then added to the 3' end of the cDNA using Terminal Deoxynucleotide Transferase (TdT). Tailed cDNA can be directly amplified by PCR using a nested gene-specific and a deoxyinosine-containing anchor primer. For the analysis of the 3' end of the alarin mRNA RT-PCR with an anchored primer at the polyA-tail and an alarin specific forward primer are used. Alternatively the 3' RACE protocol of the Gene racer kit can be used to achieve full length alarin mRNA information.

Production of Alarin and GALP Specific Antisera

In order to verify that this splice variant is translated to the peptide alarin, a specific polyclonal antibody to alarin was generated. Two antisera were custom made using the synthetic alarin peptide 6-25 (Neosystems). This region of the peptide was chosen because the first 5 amino acids of the peptide are identical with the first 5 amino acids of GALP and were omitted to exclude cross-reactivity of the alarin antibody with GALP. Cross-reactivity of the alarin antiserum with GALP and galanin was tested by dot blot analysis (FIG. 8, dot blot analysis of specificity of alarin (6-25) anti serum). To further exclude cross-reactivity in immunohistochemistry the antisera were purified via the immunogenic peptide which was coupled to NHS-activated HP columns (Amersham Biosciences) according to the manufacturer's instructions. The affinity-purified antiserum was again tested for specificity in dot blot experiments (FIG. 8).

No cross reactivity even at high concentrations of GALP and galanin was observed. The pre-immune serum also showed no specific staining in IH. The detection limit of the antiserum in dot blot and Western blot experiments was >10 fmol of synthetic peptide.

Immunohistochemistry

Figure 2:
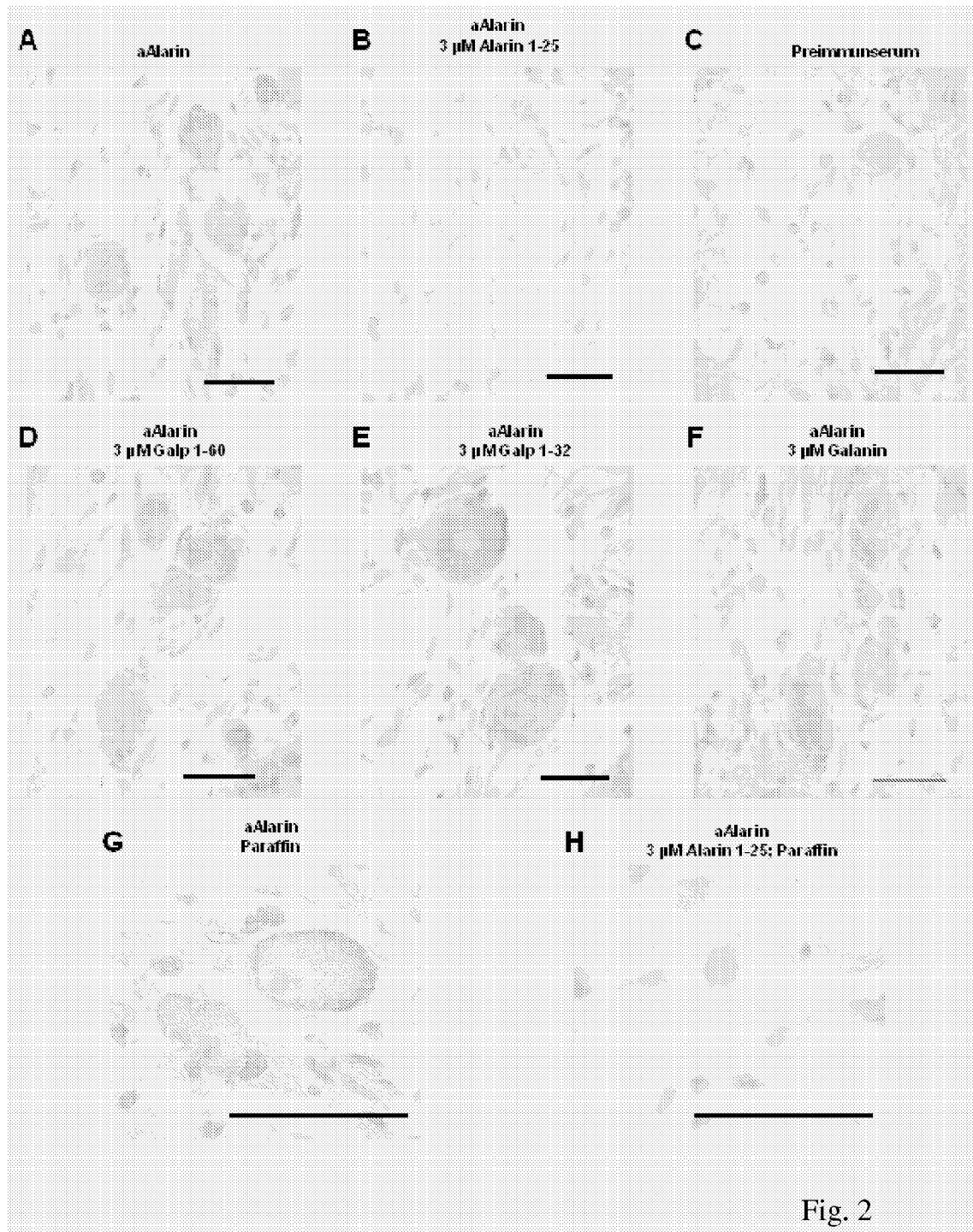

Human tissue specimens are analysed utilising chromogenic IH and/or IF techniques either on frozen or paraffin-embedded tissue sections according to standard procedures (Berger et al., 2002, 2003). Tissue samples are investigated by IH for alarin and GALP expression, PGP9.5 as neuronal marker and antibodies specific for different types of cells to determine the cell types expressing alarin. The specificity of alarin and GALP staining will be confirmed by pre-absorption of the antisera with the respective human peptides prior incubation of the tissue sections and by using non-immune rabbit serum (FIG. 2 shows IH of a ganglioneuroma tissue (stage 1, female, 2 years); A,B, D).

Preparation of Tissue Extracts

For the detection of alarin by MS and the determination of alarin concentrations by ELISA, tissues extracts are (partially) purified. For MS analysis the sample preparation have to be as pure as possible with a minimum content of about 100 fmol/µl of the peptide. An anti-alarin antibody column is generated with the affinity-purified alarin antiserum and this column is used to bind alarin peptide from tissue culture supernatants. The supernatant of cell lines is used, which show alternative alarin mRNA splicing. Peptides are eluted from the column by acidification. Fractions will be freeze-dried and analysed by MS (see below). Samples for detection of NP concentration are extracted as other neuropeptides like galanin with 1 M acetic acid and subsequent concentration by using reverse phase cartridges (Berger et al., 2002). After extraction, the samples are dried and resuspended for ELISA analysis using the rabbit antiserum specific for human alarin.

Mass Spectrometry

For MS analysis about 100-200 fmol of alarin is needed for the detection of the peptide. Considering the concentration of galanin in cell culture supernatants after 24 hrs of galanin expressing human cells (Berger et al., 2002; Kofler et al., 2004), the supernatant of one confluent T125 flask contains enough alarin. Since there is no limit of the loading volume to an antibody column, even ten to twenty times more liquid could be run over the column to obtain enough peptide for MS analysis. For desalting of the peptide solution a C18 tip (Gilson) is used. Alternatively, samples are analysed by LC/MS, using a Micromass Ultima Global mass spectrometer coupled online with a capillary reverse phase HPLC. Peptides eluting from the reversed phase column are identified either by mass and/or by sequence information obtained by CID (collision-induced dissociation). The lower detection limit of this method usually is around 50 fmoles.

Western Blot Analysis

Western blot protocol was established to detect synthetic alarin, with a detection limit of 10 fmol synthetic peptide: After separation of the sample on a 16% SDS-PAGE the gel is blotted in a tris/glycine/methanol/SDS buffer onto a PVDF membrane. After blocking of the membrane with membrane blocking agent (Amersham Bioscience) in TBS/Tween 20, the membrane is incubated with the affinity purified alarin antibody (1:500). After washing and incubation with the second antibody (Goat Anti Rabbit IgG Alkaline Phosphatase (H+L); Pierce; 1:10 000) chromogenic detection is carried out. Once tissues or cell lines showing high levels of alarin RNA or immunostaining are identified, extracts are prepared and loaded either directly or after immunprecipitation on SDS gels for Western blotting.

ELISA

To measure the concentration of alarin and GALP, ELISAs using polyclonal antisera are established. The sensitivity of the assays is in the range of other neuropeptide ELISAs (<10 fmol per well). RIA assays depend on radioactive labelled peptides, which are very expensive, are to be considered, if an ELISA test system with sufficient sensitivity is not producible with given antibodies. The blood and liquor samples are collected into chilled tubes containing EDTA and the protease inhibitor aprotinin. Blood samples are centrifuged and the plasma is stored at −70° C. until analysis. Extraction is carried out as above.

Analysis of mRNA Expression Levels by RT-PCR

Quantitative real time RT-PCR with alarin and GALP specific primers/probes are used to detect the level of differential splicing of the GALP gene. Different human cell lines and tissues, positive by alarin and/or GALP immunohistochemistry are analysed to detect the level of production of alarin mRNA. Primers corresponding to the exon 2/3 and exon 2/4 crossing are used in combination with a reverse exon 5 primer. Alternatively, an exon 2-5 fragment is amplified and uses exon 2/3 and exon 2/4 Taqman Probes for discrimination of the two splice variants. 18 sRNA serves as internal control as a housekeeping gene.

In addition, murine, rat and macaque RNA samples from different tissues are tested by RT-PCR for the expression of the alarin splice variant. Primers spanning exon 1 or 2 to 5 or 6 are used to detect the alarin splice variant and other potential splice variants.

In situ Hybridisation (ISH)

To localise the expression of alarin in comparison to GALP on the cellular level ISH with oligonucleotide probes specific for the exon-exon boundaries of alarin (exon2/4) and GALP (exon 2/3 or 3/4) is performed on the fresh frozen tissue samples. Tissue handling and treatment are carried out in order to achieve a high penetration of probes into the tissue while retaining the target nucleotide sequence at its native sites within the section. Therefore, total exclusion of tissue fixation is compared with tissue sections fixed by immersion in formalin. Dagerlind et al. (1992) found that no tissue fixation was necessary for strong and specific ISH independent of the use of radiolabel led and alkaline phosphatase labelled probes. Different pre-treated slides with ProbeOn, Silane and Poly-Llysine are tested to give minimal background. First nonradioactive labelling with biotin residues is used. If the ISH signal is weak with chromogenic detection, a signal amplification by catalysed reporter deposition (CARD) is used (Speel et al., 1999). Another possibility is the use of digoxigenin labelling and immunologic detection with alkaline phosphatase conjugated anti-digoxigenin antiserum (Boehringer Mannheim).

Receptor Autoradiography

Labelling of the Peptide

Several methods are used to label peptides with 125Iodine. Since oxidative damage during the labelling procedure or radioactive induced decay is possible, different labelling procedures have to be considered.

Histidine Labelling

The alarin peptide has a histidine residue at position 4 which can be the target of 125Iodine labelling with chloramine T (Hunter et al., 1962). 125I-alarin will be purchased as custom labelled peptide from Amersham Bioscience, which will be quite expensive but will have the advantage that the labelled peptide will have a high average specific activity (>2000 Ci/mmol). Such a high specific activity will not be achieved by in house labelling methods using choramine-T (histidine labelling) or Bolton Hunter (lysine labelling) reagents with subsequent purification over a size exclusion column to remove the excess of labelling reagent. Without HPLC purification only a specific activity <1000 Ci mmol would be achieved.

Lysine Labelling

The lysine residue at position 15 of the alarin peptide could be target of Bolton Hunter labelling (Pierce) (Bolton et al., 1972). Bolton Hunter labelling is offered also by Amersham.

Labelling on Tyrosine Residues

No tyrosine residue is present in the alarin peptide. However, a tyrosine residue could be added to a newly synthesised alarin peptide for labelling with IODO-GEN iodination reagent (Pierce), a mild solid phase oxidation reagent. Alternatively, labelling of a newly synthesised alarin peptide by incorporation of a 3H or 14C labelled amino acids is also a suitable method.

Autoradiography

Cryostat sections of freshly frozen tissue will be incubated with $^{125}$I-alarin. After the sections are rinsed and dried they will be covered with a photo emulsion (Berger et al., 2003). Specific alarin binding will be blocked by addition of an excess of non-radioactive alarin peptide. Alternatively, Receptor Binding Assays Frozen tissue samples are homogenised in homogenisation buffer using an Ultra Turax. Cells are harvested, washed with PBS and disrupted in a hypotonic HEPES buffer. After removal of cell debris, plasma membranes are recovered by high speed centrifugation. Membrane pellets are resuspended and stored at −70° C. until further use. Ligand binding assays on membrane preparations of tissues and cell lines are performed by using 125I-alarin. Non-specific binding is determined by displacement with an excess of unlabelled peptide. Once a tissue or cell line is found to bind alarin, the affinity of alarin to its receptor is determined by competitive binding experiments using a single concentration of the radioligand and various concentrations of unlabeled competitor (IC50). Saturation binding experiments specify the number of sites, Bmax and the ligand affinity Kd.

Measurement of Extra-Cellular Acidification Rate

The extra-cellular acidification rate of various human cell lines of neuronal and neuroendocrine origin are determined by using a cytosensor microphysiometer (Molecular Devices) as has been described for different human cell lines expressing galanin receptors upon stimulation with galanin:

After reaching confluency the cells are harvested and seeded into 3.0 µm pore transwells (Corning Costar) held in 12 well plates one day before the experiment. The cells are allowed to settle down in the culture medium and cultured overnight in serum-free growth-medium. The ECAR of cells is determined by using a Cytosensor Microphysiometer (Molecular Devices). A capsule spacer and a capsule insert are assembled in the transwells, transferred into a sensor chamber and kept in DMEM without sodium bicarbonate throughout the entire experiment at 37° C. The running medium is pumped through each sensor chamber at 50 µl min$^{-1}$. A typical pumping cycle of 120 s consists of a flow period of 90 s, followed by a flow-off period of 30 s. During flow-off periods, protons released from the cells accumulate in the sensor chamber, and the rate of proton release is quantified by fitting the sensor data to a straight line with the least-squares fit to the slope of the pH profile. Agonists or other agents are diluted into running medium and perfused through a second fluid path. An overall analysis of variance (ANOVA) with Tukey's post test is performed on individual time points to determine statistical significance and curve fitting is carried out using Prism™ 2.0 software (GraphPad Software Inc.).

Expression of Alarin

In addition to the coexpression of GALP and galanin mRNA in neuroblastic tissues, a smaller PCR fragment as expected was observed when GALP primers spanning exon 2-5 were used (FIG. 1A) in the RT-PCR analysis. Sequencing of the PCR products revealed differential splicing of the GALP mRNA with exclusion of exon 3 (FIG. 1B). This leads to a frame shift leading to a novel peptide sequence and a stop codon after 49 amino acids (FIG. 1C). The signal sequence of pre-pro GALP and the first 5 amino acids of the mature GALP peptide are still present and then 19 amino acids follow which do not show any homology to any other protein found in the data bases. Searching the human and murine EST databases did not reveal any EST clones corresponding to this transcript. The novel peptide was termed "ALARIN" because of the N-terminal alanin and the C-terminal serine.

Immunohistochemistry of Alarin

Figure 3:
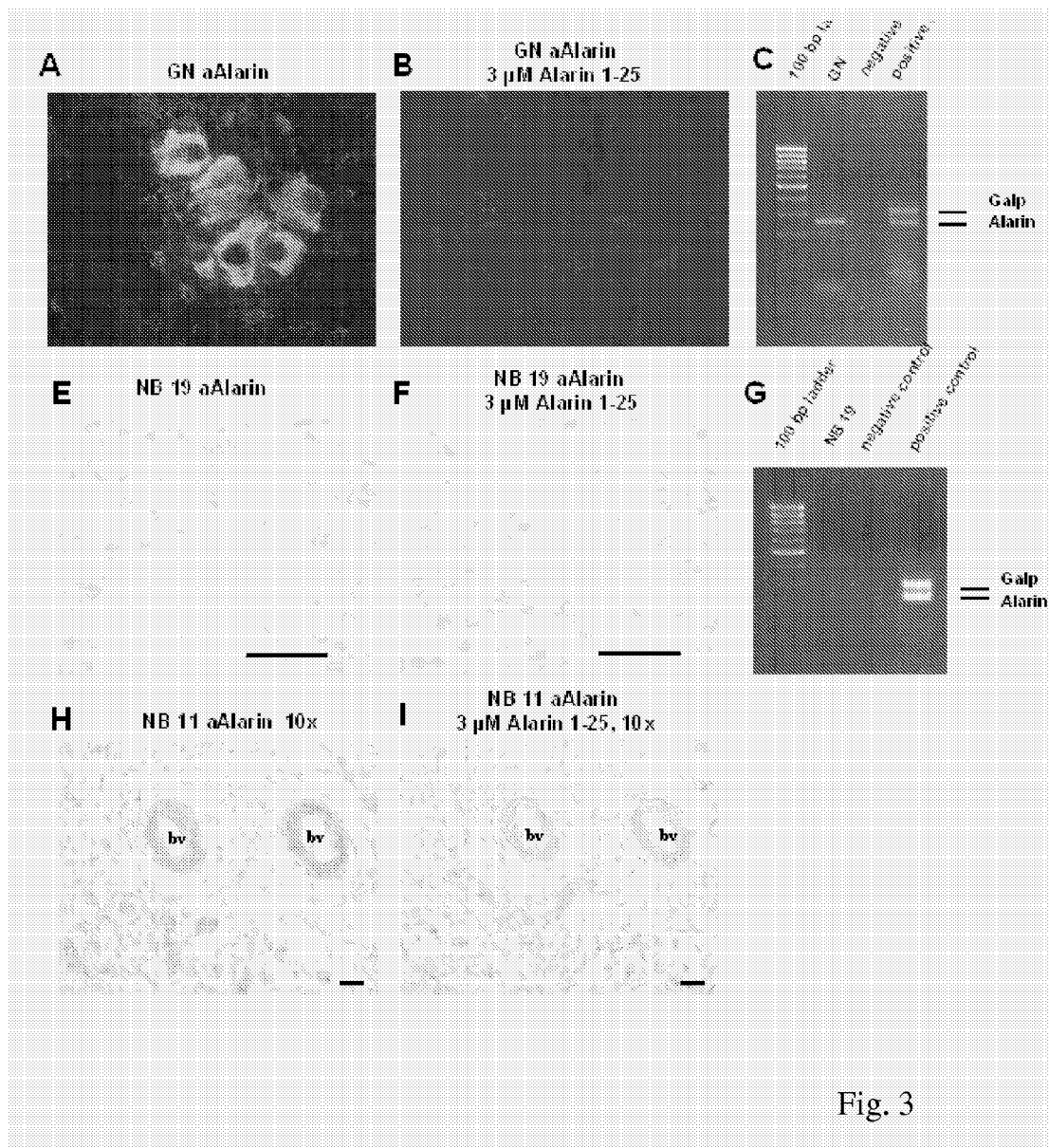
Figure 4:
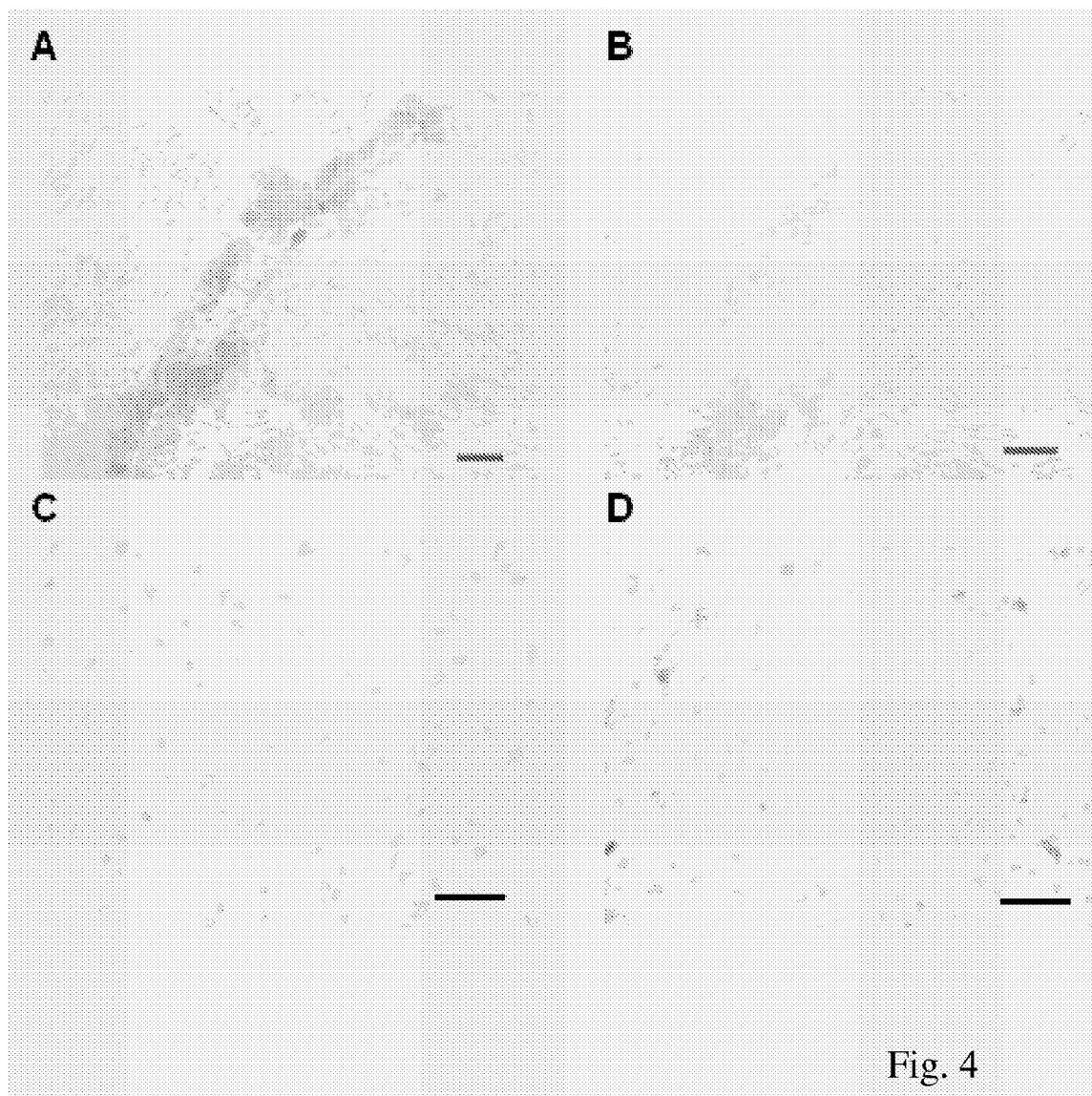

In order to verify that this splice variant is translated to the peptide alarin a (rabbit) specific polyclonal antibody to alarin was generated against amino acids 6-25 of the alarin molecule and affinity purified over an alarin (6-25) affinity column. These antibodies did not cross-react with galanin and galanin-like peptide. Detection limit of these antibodies was >10 fmoles (using synthetically produced alarin in Western blots), which is sufficient to analyse tissue extracts and cultivated cells for neuropeptides. Of course, antibody preparations with lower detection limits are easily producible by standard techniques for the preparation of poly- or monoclonal antibodies. Since differential splicing was detected in the human neuroblastoma cell line SH-SY5Y, several neuroblastic tumors were analysed with the alarin specific antibody. Immunohistochemical analysis revealed specific positive staining of this alarin antibody of several peripheral tissues in neuronal structures (FIGS. 2-4), especially of ganglia in ganglioneuromas and neuroblastomas (FIGS. 2-3). With a higher resolution, also a specific localisation of the peptides in vesicles in the neighbourhood of the cell membrane is observed in the microscope, which again shows the neurohormone character of alarin. The cytoplasmic staining could be abolished by pre-incubation of the antibody with 1 µM synthetic alarin. CNS IH data show an expression of alarin in various human tissue, especially in the cerebellum and pituitary. Further positive immunohistochemistry was observed e.g. in blood vessels (partially), which shows connection to blood pressure regulation, or ganglia in colon, showing relevance in colon motility. These data show that differential splicing of GALP mRNA results not only in translation of GALP peptide but also in expression of the novel neuropeptide alarin. Since alarin lacks the homology to galanin it is clear that alarin does bind to different receptors and therefore exerts different functions as galanin and GALP. Two reasons why alarin has not been detected by other investigators so far are: firstly, expression of GALP has been investigated by immunohistochemistry (IH) and the antibody used from amino acid 1-10 might not cross-react with the first five amino acids of alarin and even if it does, no discrimination could have been seen between the two peptides. Secondly, in situ hybridisation also will detect alarin and GALP mRNA if a probe is used which is spanning several exons, but cannot distinguish between the two.

Alarin Does Not Bind to Galanin Receptors

Binding assays and functional microphysiometry were performed to investigate whether alarin binds to galanin receptors or not. The results of these tests clearly showed that binding of alarin to galanin receptors can be excluded (FIG. 9; microphysiometry using human neuroblastoma). This shows that the function of alarin is different from galanin or galanin-like peptide.

Alarin Sequences of Various Animals Show Homology

Alarin sequences obtained from humans, macacqe, mouse and rat are of equal length and share high homology (>80% identity) in the first part (first 10 amino acids), in the second part (amino acids 11 to 20) human and macacqe show high homology (as well as mouse and rat). In the last part (residues 21 to 25), again high homology (>80% identity) between all four types of alarin is given:

TABLE 1

| Amino acid sequence alignment | | | | |
|---|---|---|---|---|
| APAHRSSTFP | KWVTKTERGR | QPLRS | human | (SEQ ID NO: 1) |
| ----Q----- | ------G--- | ----- | macacqe | (SEQ ID NO: 11) |
| -------P-- | PRP-RAG-ET | -L--- | mouse | (SEQ ID NO: 9) |
| ---------- | QRP-RAG-QT | -L--- | rat | (SEQ ID NO: 10) |

Differential Splicing Alarin/GALP is Individually Regulated in Various Cell Types Induction of mRNA was performed by application of an protein kinase C activator (phorbol 12-myristate 13-acetate; PMA), a known inductor of the mRNA of several neuropeptide including galanin and GALP mRNA.

Figure 7:
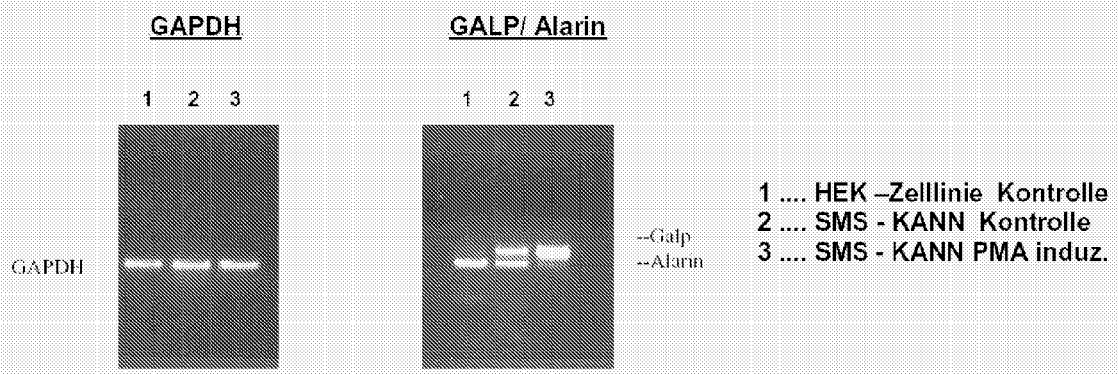
FIG. 7 shows individual regulation of differential splicing of alarin/GALP in various cell types.
Figure 7:
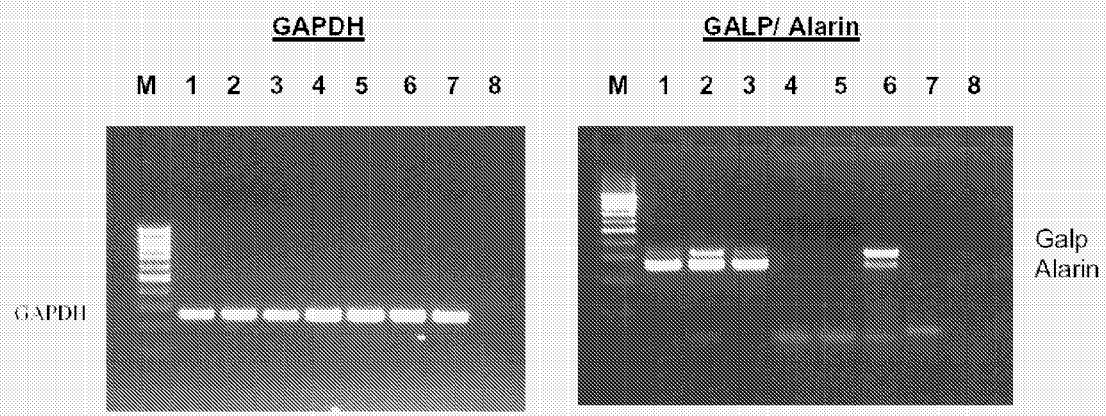

After PMA [50 nM] treatment predominantly GALP mRNA is produced in neuroblastoma cell line SMS-KAN (FIG. 7, upper part); in human embryonic liver cells (HEK) predominantly alarin mRNA is produced. In mice, alarin splice variant was found in thyroid gland and brain. In macacqe, alarin was found in brain tissue.

Alarin in Pyramidal Cells of the Cortex

Figure 6:
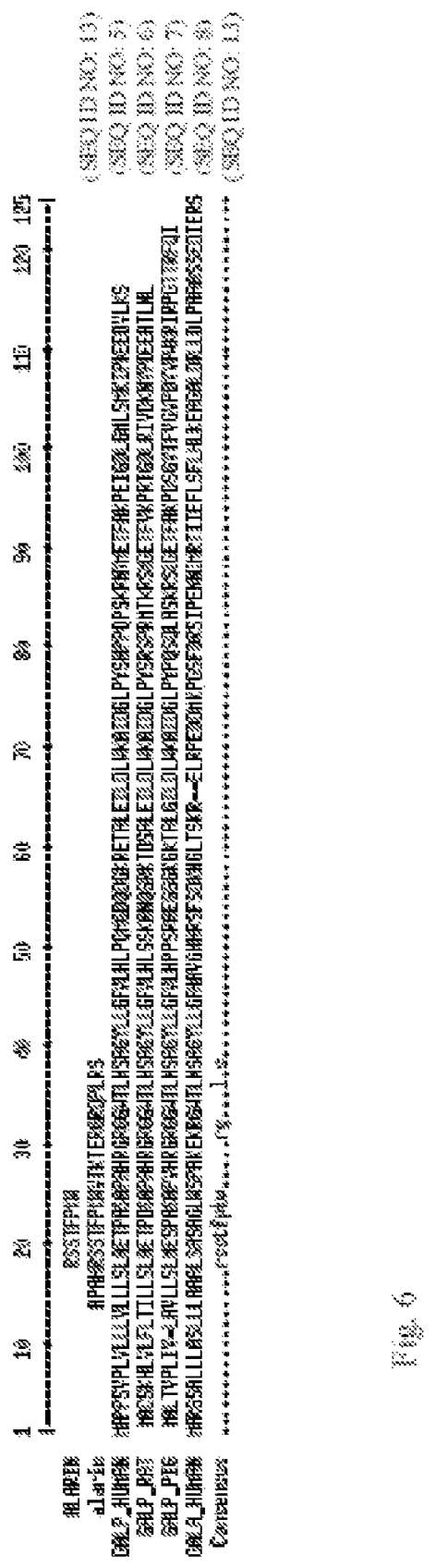

Alarin could be specifically identified in pyramidal cells of the cortex (FIG. 6). A weaker immunoreactivity was found in cerebellum. This further shows the function of alarin as a neuropeptide with a different function than GALP.

Oncology: Neuroblastic Tumors

Immunohistochemistry with antibodies directed against synthetic alarin peptide detected specific cytoplasmic granular staining in ganglia of human ganglioneuroma and ganglioneuroblastoma as well as differentiated tumor cells of neuroblastoma tissues. Undifferentiated neuroblasts of these tumor tissues did not show alarin-like immunoreactivity and alarin specific mRNA (FIGS. 3 and 10). These findings show that alarin expression is a feature of ganglionic differentiation in neuroblastic tumor tissues.

Skin/Dermatology

In the skin, various diseases such as atopic dermatitis, urticaria, psoriasis, diseases of the pilosebaceous unit, the growth of skin tumors, but also physiological processes (pigmentation, hair growth, angiogenesis or wound healing a.o.) have been demonstrated to be associated or affected by neuromediators. Most of the above diseases are frequent in our society with a high socio-economic factor. During the last few years, a modern concept of an interactive and interdependent network between the cutaneous neurological system, the neuroendocrine axis and the immune system has been established. Data available at present very clearly indicate that neuromediators influence a variety of physiological and pathophysiological functions including cellular development, growth, differentiation, immunity, inflammation, pigmentation, vascular biology and wound healing.

From a functional aspect, one of the most important features of the skin immune system is its capability of responding to exogenous or endogenous stressors including ultraviolet irradiation, bacterial infection, heat, chemicals, allergens or mechanical trauma. Usually, the innate immune system generates an inflammatory response that tries to neutralize the stressor, and in parallel activates an adaptive immune response.

Localisation

Alarin is detected in the human and murine epidermis, around hair follicles, sweat glands and blood vessels (FIG. 11; blood vessels; murine skin). Accordingly, alarin mRNA is detectable in cultured human keratinocytes.

Skin-Inflammation

The distribution of alarin around blood vessels in human and murine skin shows a vascular function. Co-injection of alarin peptide with substance P and CGRP showed an inhibition of inflammatory oedema in murine dorsal skin (FIG. 12; inflammatory oedema).

Eye/Ophtalmology

Human: Alarin is detected in ganglia of the retina, cornea and the optical nerve of the human and murine eye. (FIG. 13; human eye).

Blood-Neutrophils/Immunology

Staining of human tissue with blood vessels filled with different types of blood cells indicates that alarin is present in polymorphonuclear neutrophils (FIG. 14; blood cells).

Brain/Regulation of Neuroendocrine Functions

Localisation

Human: Specific Alarin-LI is detected in cell populations of the pituitary (FIG. 15; pituitary).

Body Weight

Intact adult male mice (C57Bl/6) were treated by a single injection into the lateral ventricles with either artificial cerebrospinal fluid (aCSF), alarin 1-25 (A1), alarin 3-25 (A3). Alarin 3-25 showed a significant reduction of body weight one hour after injection (FIG. 16; body weight).

Food Intake

Intact adult male mice (C57Bl/6) were treated by a single injection into the lateral ventricles with either artificial cerebrospinal fluid (aCSF), alarin 1-25 (A1), alarin 3-25 (A3). Alarin 3-25 showed a significant decrease of food intake one hour after injection (FIG. 17; food intake).

Lutenising Hormone (LH) Secretion

Intact adult male mice (C57Bl/6) were treated by a single injection into the lateral ventricles with either artificial cerebrospinal fluid (aCSF), alarin 1-25 (A1), alarin 3-25 (A3). Alarin 3-25 showed a significant increase of plasma LH levels (FIG. 18; LH content).

Alarin Receptor

The lack of the galanin binding domain in the alarin peptide together with binding assays on galanin receptors and microphysiometry (FIG. 9; Microphysiometry) on galanin receptor expressing cells indicates that alarin is not able to activate these receptors.

The first two amino acids of human and murine alarin could be potentially removed by dipeptidyl dipeptidase IV. Therefore, functional assays were carried out with the amidated synthetic murine alarin peptides 1-25 and 3-25. Alarin 1-25 was more potent in inhibition of oedema formation in the skin. In contrast, only alarin 3-25 was active in the CNS.

These data show the existence of at least two different receptor subtypes, one which is activated by the full length peptide and one which is activated by alarin 3-25.

Materials and Methods

RT-PCR Analysis

Total RNA (1 μg) was reverse-transcribed with 200 U SUPERSCRIPT II reverse transcriptase (Life Technologies Inc., Gaithersburg, USA). 100 ng cDNA was used for PCR amplification using Thermo Start polymerase (ABgene, Surrey, UK) in the presence of 10 pmol of each primer. The primers used were as follows: GALP: Acc. No.: NM_033106; (66-84, 376-357) and for GAPDH Acc. No.: NM_002046; (391-414, 644-621). For the GAPDH RT-PCR a initial penetration step at 95° C. for 5 min was performed, followed by 30 cycles of 95° C. for 30 s, 62° C. for 30 s and 72° C. for 30 s and a final extension of 72° C. for 2 min. GALP RT-PCR's were performed with a denaturation step at 95° C., followed by 50 cycles each consisting of 10 s at 95° C., a primer annealing step at 55° C. for 30 s and 72° C. for 30 s, and a final extension step at 72° C. for 10 min. The PCR products were analyzed by electrophoresis on an agarose gel.

Generation of Polyclonal Alarin Antibodies

Rabbit polyclonal antiserum were custom made using the synthetic human alarin peptide 6-24-Cys (SSTFPKWVTK-TERGRQPLRC) or murine synthetic alarin peptide 6-24-Cys (NeoMPS, Inc.; Strasbourg, France). Briefly, alarin 6-24 was coupled via a C-terminal cystein residue to the carrier protein key-hole limpet hemocyanin (KHL). Immunization was carried out on day 0, 14, 28 and 56.

For affinity purification of the antiserum the immunogenic peptide alarin 6-24-Cys (4 mg) was coupled to a HiTrap NHS-activated HP column (1 ml) according to the manufacturer's instructions (Amersham Biosciences; Buckinghamshire, UK). The polyclonal anti-alarin antiserum (4 ml) of the final bleeding was diluted 1:1 with phosphate buffered saline (PBS), filtered through a 0.45 μm filter and loaded onto the column. The column was washed with 50 mM Tris-HCl pH 8, 0.1% TritonX-100, 500 mM NaCl, followed by 50 mM Tris-HCl pH 9, 0.1% TritonX-100, 500 mM NaCl and finally 50 mM sodium phosphate pH 6.3, 0.1% TritonX-100, 500 mM NaCl. The antibody was eluted with 50 mM glycine pH 2.5, 0.1% Triton X-100, 0.15 M NaCl and the eluate was immediately neutralized with 20 mM Tris-HCl pH 9.

Immunohistochemistry

Cryosections (10 μm) of the tissues were air dried, fixed in 4% formaldehyde for 10 min and washed with 1×PBS. Immunostaining was performed according to the protocol of Level 2 USA Ultra Streptavidin Detection System (Signet Laboratories, Inc., Dedham, USA) with modifications. The endogenous peroxidase was quenched in 3% $H_2O_2$ for 5 min. Sections were incubated with blocking reagent for 30 min at room temperature followed by an overnight incubation at 4° C. with the affinity purified alarin antibody, diluted 1:200 in PBS. After three washes with PBS and incubation with linking reagent for 1 hr, sections were treated with labeling reagent for 20 min and washed with PBS. Alarin-like immunoreactivity (alarin-LI) was visualized using 3,3'-diaminobenzidine as a chromogenic substrate. Sections were counterstained with Mayer's Hemalum solution (Merck, Darmstadt, Germany) and mounted with Kaiser's glycerol gelatin. The specificity of the immunostaining was tested by pre-absorption of the affinity purified alarin antiserum with 3 μM of the respective peptide, for 2-3 h at 37° C. Following centrifugation for 10 min at 13000 rpm serial sections were incubated with the preabsorbed serum.

For alarin immunofluorescence, cryosections (10 μm) were air-dried for 15 min at room temperature, fixed in 4% formaldehyde for 10 min, washed with 1×PBS and blocked with 3% normal goat serum in PBS for 30 min. The sections were incubated overnight at 4° C. with the alarin antibody diluted 1:100 in 3% normal goat serum in PBS. After several rinses with PBS, the sections were incubated for 1 hour at room temperature with Cy2-linked goat anti-rabbit antibody (1:100, Amersham Pharmacia, Buckinghamshire, UK). After several washes with PBS and Aqua bidest. the sections were mounted with Aqua Polymount (Polysciences, Inc., Warrington, USA) and examined with a fluorescence-equipped microscope. Paraffin sections (4 μm) were deparaffinized, rehydrated and heated to 90° C. for 15 min in 0.01 M citric acid buffer (pH 6.0). The sections were washed with 1×PBS, blocked with 3% normal goat serum in PBS for 30 min and then treated as the cryosections.

Measurement of Inflammatory Oedema Formation

Experiments involving mice were carried out under the Animals (Scientific Procedures) Act, 1986. Normal female CD-1 mice (22-27 g, 8-12 weeks) were obtained from Charles River, U.K. All mice were maintained on normal diet, with free access to food and water, in a climatically controlled environment. Animals were anaesthetized with urethane (25% w v-1; 2.5 g kg-1 i.p.) and the dorsal skin was shaved. Injection sites were chosen according to a randomized site pattern on the dorsal skin of the anaesthetized mouse. Agents were from Sigma, Poole, U.K., unless specified. Alarin (1-25)-amide (murine) alarin (3-32)-amide (murine) were custom synthesized by NeoMPS Inc. (Strasbourg, France). All peptides were dissolved in distilled water. The stock solutions (10 nM) were stored at −20° C. and further diluted in Tyrode's solution (137 mM NaCl, 2.7 mM KCl, 0.5 mM MgCl2, 0.4 mM NaH2PO4, 11.9 mM NaHCO3, 5.6 mM glucose) just prior use.

Plasma extravasation was used as an index of inflammatory oedema formation and measured as previously described (Cao et al, 1999). Briefly, test agents were diluted in Tyrode's solution and stored on ice. 125I-bovine serum albumin (BSA) (45 kBq in 100 μl of saline) was administered intravenously (i.v.) into the tail vein and 5 min later test agents (50 μl/site) were injected intradermally (i.d.). Plasma extravasation was allowed for 30 min and then a blood sample (0.5 ml) was obtained via cardiac puncture and centrifuged at 10 300 g for 4 min to obtain plasma. The mice were then killed, the dorsal skin was removed, and the injected sites punched out (8 mm). The amount of plasma extravasated (μl g-1 tissue) was calculated by comparing the amount of radioactivity in each skin site with that in 100 μl plasma from the same animal.

Measurement of Extracellular Acidification Rate

SH-SY5Y/GalR1 and SH-SY5Y/GalR2 cells (Berger 2004) were seeded into 3.0-μM pore size Transwells (Corning Costar, Cambridge, Mass., USA). The extracellular acidification rate was determined using a cytosensor microphysiometer (Molecular Devices, Ismanning, Germany) as previously reported (Lang et al., 2001).

Receptor Binding Assay

Membrane preparations and radioligand binding assays were performed according to Berger et al. (Berger et al., 2002). Displacement of radiolabeled GAL binding to membrane preparations (15 μg) was carried out in duplicates in a total volume of 120 μl of binding buffer containing 50 pM [125I]GAL (2,000 Ci/mmol; Amersham Pharmacia Biotech (Little Chalfont, UK) and different concentrations of synthetic murine alarin (1-25-amide) and alarin (3-25-amide).

Body Weight

Intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Body weight and food weight were measured at 1 hr, 2 hr, and 24 hr post injection. (Shown here as percent change in body weight from baseline).

Food Intake

Intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Body weight and food weight were measured at 1 hr, 2 hr, and 24 hr post injection. (Shown here as grams of food consumed).

Lutenising Hormone Levels

Intact adult male mice (C57Bl/6) were treated by a single injection into the lateral ventricles with either artificial cerebrospinal fluid (aCSF), alarin 1-25 (A1), alarin 3-25 (A3). Each treatment was given in an equimolar dose of 5 nmol. Blood was collected 30 min after injection and serum was assayed for LH content. (LH levels shown here in ng/ml).

Pharmaceutical Preparations Comprising the Polypeptides or Antibodies According to the Present Invention:

The polypeptides or antibodies according to the present invention, especially alarin, or alarin fragment or a specific alarin antibody (all: as defined above) may be provided as a pharmaceutical preparation, preferably admixed with a suitable pharmaceutically useable carrier, diluent and/or excipient. These preparations may contain further ingredients depending on the intended use or mode of administration.

Sequences:

```
>Alarin peptide
RSSTFPKW

>Alarin
                                             (SEQ ID NO: 1)
APAHRSSTFP KWVTKTERGR QPLRS >PUR9_MYCPA swissprot|Q9RAJ5|PUR9_MYCPA
                                             (SEQ ID NO: 2)
MSTDDWRENA KRPIRRALIS VYDKTGLVEL AQGLTEAGVE

IVSTGSTAKV IAEKGIPVTR VEVLTGFPEV LDGRVKTLHP

RVHAGLLADL RKPEHAAALE QLGIAAFELV VVNLYPFTET

VDSGAGIDEC VEQIDIGGPS MVRAAAKNHP SVAVVVDPLG

YDGVLAAVRH GGFTLAERKR LAALAFQHTA DYDIAVATWM

ESTLAPEHPP TTFPKWLGRS WRRSAMLRYG ENPHQQASLY

SDPGAWPGLA QAEQLHGKEM SYNNFTDADA AWRAAFDHEQ

TCVAIIKHAN PCGIAISSIS VADAHRKAHE CDPLSAFGGV

IAANTEVSVE MAEYVSTIFT EVIIAPAYQP AALEILTRKK

NIRVLVASEP LTGGTELRPI SGGLLVQQRD ELDAHGDNPA

NWTLATGAPA DPATLADLVF AWRVCRAVKS NAIVIAAGGA

TIGVGMGQVN RVDAARLAVE RGGDRVRGAV AASDAFFPFP

DGLETLTGAG VKAVVHPGGS VRDDEVTAAA ANAGITLYLT

GARHFAH

>VSN1_NOCAE swissprot|P50186|VSN1_NOCAE
                                             (SEQ ID NO: 3)
MSDKSSRAAA RARAHASGTY PAPLNAGRSR NMQANRRSGT

KPEAALRSAL FKLGYRYRKD FLLRLGDGVK VKPDIVFTAR

KVAVFIDGCF WHVCPDHGRQ PTTNEWYWSP KLRRNVERDR

TVNQSLTNAG WRVLRVWEHE ELQDAVAAVV DTLHHLEHGF

DTSAED

>Alarin-Precursor
                                             (SEQ ID NO: 4)
MAPPSVPLVL LLVLLLSLAE TPASAPAHRS STFP

KWVTKTERGR QPLRS

>GALP_HUMAN swissprot|Q9UBC7|GALP_HUMAN
(GALP precursor)
                                             (SEQ ID NO: 5)
MAPPSVPLVL LLVLLLSLAE TPASAPAHRG RGGWTLNSAG

YLLGPVLHLP QMGDQDGKRE TALETLDLWK AIDGLPYSHP

PQPSKRNVME TFAKPEIGDL GMLSMKIPKE EDVLKS

>GALP_RAT swissprot|Q9QXQ6|GALP_RAT
(GALP precursor)
                                             (SEQ ID NO: 6)
MACSKHLVLF LTILLSLAET PDSAPAHRGR GGWTLNSAGY

LLGPVLHLSS KANQGRKTDS ALEILDLWKA IDGLPYSRSP

RMTKRSMGET FVKPRTGDLR IVDKNVPDEE ATLNL

>GALP_PIG swissprot|Q9TT95|GALP_PIG
(GALP precursor)
                                             (SEQ ID NO: 7)
MALTVPLIVL AVLLSLMESP ASAPVHRGRG GWTLNSAGYL

LGPVLHPPSR AEGGGKGKTA LGILDLWKAI DGLPYPQSQL

ASKRSLGETF AKPDSGVTFV GVPDVVPWKR IRPGTTRFQI

>GALA_HUMAN swissprot|P22466|GALA_HUMAN
(Galanin precursor)
                                             (SEQ ID NO: 8)
MARGSALLLA SLLLAAALSA SAGLWSPAKE KRGWTLNSAG

YLLGPHAVGN HRSFSDKNGL TSKRELRPED DMKPGSFDRS

IPENNIMRTI IEFLSELHLK EAGALDRLLD LPAAASSEDI ERS
```

Abbreviations
GAL galanin
GALP galanin-like peptide
NP neuropeptides
RT-PCR reverse transcription polymerase chain reaction
GalR1 galanin receptor subtype 1
GalR2 galanin receptor subtype
GalR3 galanin receptor subtype
CGRP calcitonin gene-related peptide
i.c.v. intracerebroventricular
GnRH gonadotropin-releasing hormone
IH immunohistochemistry
IF immunoflourescence
MS mass spectrometry
ISH in situ hybridisation

REFERENCES

Vrontakis (2002) Curr Drug Target CNS Neurol Disord, 1, 531-41.
Floren et al. (2000) Neuropeptides, 34, 331-7.
Tatemoto et al. (1983) FEBS Lett, 164, 124-8.
Ohtaki et al. (1999) J Biol Chem, 274, 37041-5.
Unniappan et al. (2003) Mol Cell Endocrinol, 200, 177-87.
Berger et al.(2003a) Acta Neuropathol (Berl), 105, 43-8.
Berger et al. (2002) Neuroendocrinology, 75, 130-8.
Berger et al.(2003) Acta Neuropathol (Berl), 105, 555-60.
Lang et al. (2001) Eur J Pharmacol, 423, 135-41.
Kofler et al. (2004), J. Invest. Dermatol. 122, 1050-1053.
Cunningham et al.(2002) Endocrinology, 143, 755-63.
Dagerlind et al. (1992) Histochemistry, 98, 39-49.
Speel et al. (1999) Endocr Pathol, 10, 193-198.
Hunter et al. (1962), Nature 194, 495-496.
Bolton et al. (1973), Biochem. J. 133, 529-539.

The invention claimed is:

1. An isolated polypeptide consisting of the amino acid sequence of SEQ ID No:1.

2. A fusion protein comprising a carrier protein and an isolated polypeptide consisting of the amino acid sequence of SEQ ID NO: 1, wherein the carrier protein is a marker protein, an immunogenic protein, or a transport protein.

3. A pharmaceutical composition comprising a polypeptide consisting of the amino acid sequence of SEQ ID NO: 1 and a pharmaceutical carrier.

* * * * *